US012168782B2

United States Patent
Mohamed

(10) Patent No.: US 12,168,782 B2
(45) Date of Patent: Dec. 17, 2024

(54) PHYSIOLOGICAL BIOMIMETIC CULTURE SYSTEM FOR HEART SLICES

(71) Applicant: University of Louisville Research Foundation, Louisville, KY (US)

(72) Inventor: Tamer Mohamed, Goshen, KY (US)

(73) Assignee: University of Louisville Research Foundation, Louisville, KY (US)

(*) Notice: Subject to any disclaimer, the term of this patent is extended or adjusted under 35 U.S.C. 154(b) by 348 days.

(21) Appl. No.: 17/415,239

(22) PCT Filed: Dec. 19, 2019

(86) PCT No.: PCT/US2019/067343
§ 371 (c)(1),
(2) Date: Jun. 17, 2021

(87) PCT Pub. No.: WO2020/159642
PCT Pub. Date: Aug. 6, 2020

(65) Prior Publication Data
US 2022/0064601 A1   Mar. 3, 2022

Related U.S. Application Data

(60) Provisional application No. 62/798,572, filed on Jan. 30, 2019.

(51) Int. Cl.
*C12N 5/077* (2010.01)
*G01N 33/50* (2006.01)
*G09B 23/30* (2006.01)

(52) U.S. Cl.
CPC ....... *C12N 5/0657* (2013.01); *G01N 33/5088* (2013.01); *G09B 23/306* (2013.01); *C12N 2500/02* (2013.01); *C12N 2501/115* (2013.01); *C12N 2529/00* (2013.01); *C12N 2533/30* (2013.01)

(58) Field of Classification Search
CPC .............. C12N 5/0657; C12N 2500/02; C12N 2501/115; C12N 2529/00; C12N 2533/30; G01N 33/5088; G09B 23/306
See application file for complete search history.

(56) References Cited

PUBLICATIONS

Thomas et al. A Myocardial Slice Culture Model Reveals Alpha-1A-Adrenergic Receptor Signaling in the Human Heart. J Am Coll Cardiol Basic Trans Science. 2016; 1(3):155-67. (Year: 2016).*
Kano et al. VEGF-A and FGF-2 synergistically promote neoangiogenesis through enhancement of endogenous PDGF-B-PDGFRb signaling. Journal of Cell Science. 2005; 118: 3759-3768. (Year: 2005).*
Fernández-Avilés et al. Circ Res. 2004;95:742-748. (Year: 2004).*
Kano et al. J Cell Sci. 2005; 118: 3759-3768. (Year: 2005).*
Xiao et al. Lab Chip, 2014, 14, 869-882. (Year: 2014).*
Sakaguchi et al., Scientific Reports. 2013; 3:1316, p. 1-7. (Year: 2013).*
Watson et al.; "Biomimetic Electromechanical Stimulation to Maintain Adult Cardiac Tissue in Vitro"; PhD Dissertation, Imperial College London, Jul. 2018.
Perbellini et al.; "Investigation of cardiac fibroblasts using myocardial slices"; Cardiovascular Research, vol. 114, No. 1, Jan. 1, 2018, pp. 77-89.
Kaneko et al.; "Histological Validation of Heart Slices a a Model in Cardiac Research"; Journal of Cell Science and Therapy, vol. 3, No. 4, 2012, pp. 1-5.
Fischer et al.; "Long-term functional and structural preservation of precision-cut human myocardium under continuous electromechanical stimulation in vitro"; Nature Communications, vol. 10, No. 117, Jan. 10, 2019, pp. 1-13.
Pillekamp et al.; "Physiological Differences Between Transplanted and Host Tissue Cause Functional Decoupling after in vitro Transplantation of Human Embryonic Stem Cell-Derived Cardiomyocytes"; Cellular Physiology and Biochemistry, vol. 23, No. 1-3, Feb. 18, 2009, pp. 65-74.
Kang et al.; "Human Organotypic Cultured Cardiac Slices: New Platform For High Throughput Preclinical Human Trials"; Scientific Reports, vol. 6, No. 28798, pp. 1-13, 2016.

* cited by examiner

*Primary Examiner* — Taeyoon Kim
*Assistant Examiner* — Jianjian Zhu
(74) *Attorney, Agent, or Firm* — ALGM LLP; Harry J. Guttman

(57) ABSTRACT

A method for culturing heart tissue by culturing a slice of the heart tissue in a culture medium, wherein the culture medium comprises fetal bovine serum (FBS), vascular endothelial cell growth factor (VEGF), and fibroblast growth factor (FGF); and applying electrical stimulation to the slice while the heart slice is in culture is provided. Methods of screening candidate therapeutic agents for therapeutic effect or cardiotoxicity using the culture system are also provided.

12 Claims, 11 Drawing Sheets

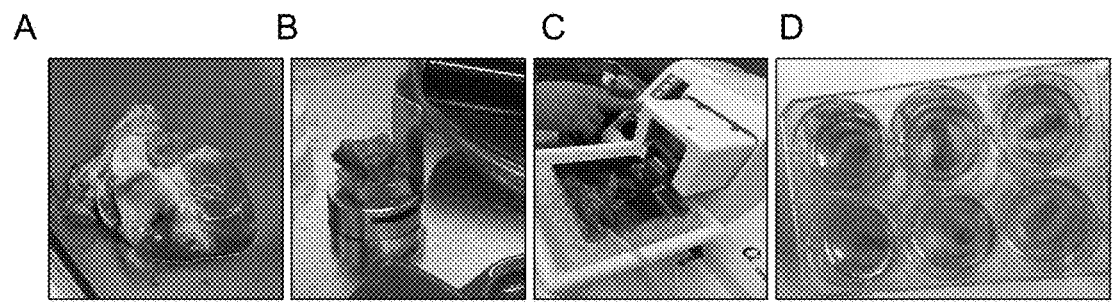
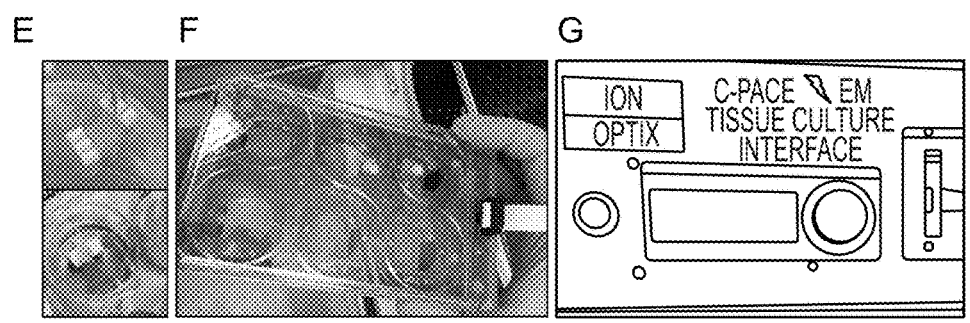
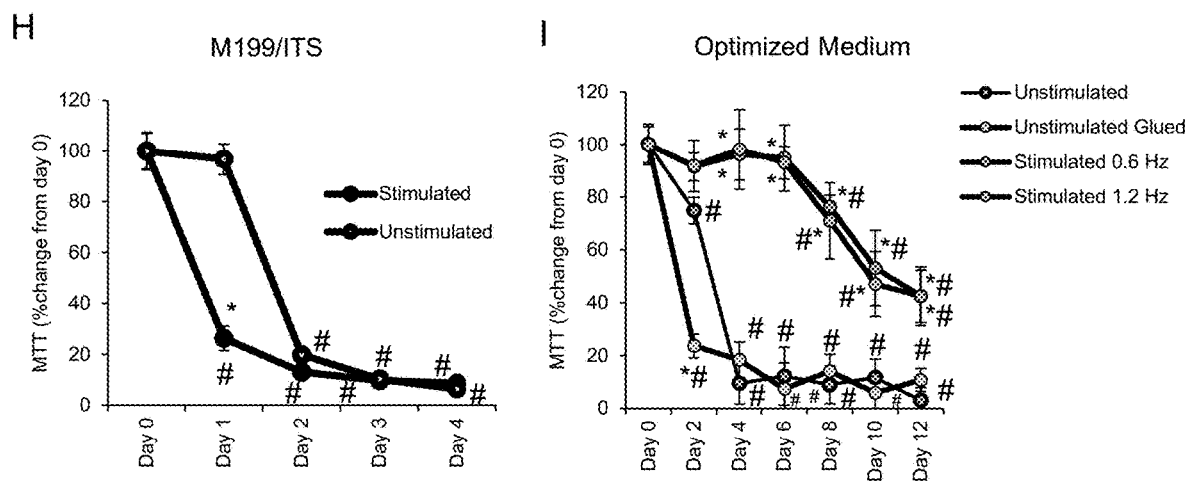
FIG. 1A-1I

PHYSIOLOGICAL BIOMIMETIC CULTURE SYSTEM FOR HEART SLICES

FIELD OF THE INVENTION

The invention is generally related to a medium-throughput culture system for heart slices which utilizes electrical stimulation and an optimized culture medium.

BACKGROUND OF THE INVENTION

Heart failure is the number one killer[1] and drug induced cardiotoxicity is a major cause of market withdrawal[2]. The lack of availability of culture systems for human heart tissue that is functionally and structurally viable for more than 24 hours limits validation of novel heart failure therapies and reliable cardiotoxicity testing. Therefore, there is an urgent need to develop a reliable system for culturing heart tissue for testing drug efficacy and toxicity. The recent move toward the use of human induced pluripotent stem cell-derived cardiomyocytes (hiPSC-CMs) in cardiotoxicity and drug efficacy testing has provided a partial solution to address this issue; however, the immature nature of the hiPSC-CMs and loss of tissue integrity compared to multicellular heart tissue are major limitations of this technology[3]. A recent study has shown that this limitation can be partially overcome if cardiac tissues are formed on hydrogels from early-stage hiPSC-CMs soon after the initiation of spontaneous contractions and are subjected to gradual increase in electrical stimulation over time[4]. However, the electromechanical properties did not achieve the maturity seen in adult human myocardium. Moreover, heart tissue is structurally more complicated, being composed of a heterogeneous mixture of various cell types including endothelial cells and various types of stromal fibroblasts linked together with a unique mixture of extracellular matrix proteins[5]. This heterogeneity of the non-cardiomyocyte cell population[6-8] in the adult mammalian heart is a major obstacle in modeling heart tissue using individual cell types. These major limitations highlight the importance of developing methods to enable culture of intact cardiac tissue for optimal studies involving physiological and pathological conditions[4].

Culturing human heart slices is a promising model of intact human myocardium. This technology provides access to a complete 3D multicellular system that is similar to the human heart tissue that reflects the human myocardium in physiological or pathological conditions, both functionally and structurally. The first culture system using an air-liquid interface was developed[9] using the transwell system and simplified medium (M199/ITS) for culturing heart slices. Even though the electrophysiological properties of the heart slices were maintained for 28 days, the heart slices lost over 90% of their ability to contract within 24 hours in culture[9]. This culture system has been used by others to culture heart slices for up to 24 hours[10-12]. Three recent studies have shown that electromechanical stimulation is paramount for maintaining heart slices in culture[13-15]. However, these studies involved highly sophisticated bioengineered devices, which may limit adoption of the technology by other laboratories. In addition, these studies used the standard simplified medium (M199/ITS), which does not support the high metabolic demands of cardiac tissue. Therefore, there is a need in the art for a culture system having optimized culture conditions and a simplified method in order to promote accessibility; and to test applications, such as gene therapy, and isolated myofibril contractility.

SUMMARY OF THE INVENTION

It is an object of the disclosure to provide an easily reproducible, heart slice culture system, which is preferably at least medium-throughput, which does not compromise the heart slice functionality for several days.

An aspect of the disclosure provides a method for culturing heart tissue, comprising culturing a slice of the heart tissue in a culture medium, wherein the culture medium comprises fetal bovine serum (FBS), vascular endothelial cell growth factor (VEGF), and fibroblast growth factor (FGF); and applying electrical stimulation to the slice while the heart slice is in culture. In some embodiments, the electrical stimulation has a frequency of 0.5 to 2 HZ. In some embodiments, the electrical stimulation has a frequency of 1.2 HZ. In some embodiments, the electrical stimulation has a voltage of 5-15 V. In some embodiments, the electrical stimulation has a voltage of 10 V. In some embodiments, a stimulation device used to apply the electrical stimulation comprises graphite electrodes.

In some embodiments, the culture medium does not include 2,3-butanedione monoxime (BDM). In some embodiments, the culture medium does not include any fatty acids added in addition to fatty acids present in the FBS. In some embodiments, the slice of the heart tissue has a thickness of 100-500 μm. In some embodiments, the culture medium is oxygenated prior to being added to the culture. In some embodiments, the method is performed for at least 2 days. In some embodiments, the culture medium is replaced with fresh culture medium at least once per day. In some embodiments, the heart tissue is obtained from a mammal.

Another aspect of the disclosure provides a method for screening candidate therapeutic agents for therapeutic effect or cardiotoxicity, comprising culturing a slice of the heart tissue in a culture medium, wherein the culture medium comprises fetal bovine serum (FBS), vascular endothelial cell growth factor (VEGF), and fibroblast growth factor (FGF); applying electrical stimulation to the slice while the heart slice is in culture; contacting the slice with a candidate therapeutic agent; and measuring one or more factors within the heart tissue that are indicative of the therapeutic effect or cardiotoxicity of the candidate drug.

In some embodiments, the step of contacting comprises adding the candidate therapeutic agent to the culture medium. In some embodiments, the step of contacting comprises infecting the slice with a virus expressing the candidate therapeutic agent. In some embodiments, the one or more factors includes at least one of measuring cardiomyocyte proliferation, measuring transverse conduction velocity, determining viability of the heart tissue, measuring the contractility of the heart tissue, measuring calcium homeostasis, measuring calcium signal propagation, measuring electrophysical properties of single cardiomyocytes, measuring action potential, and measuring mitochondrial metabolism.

BRIEF DESCRIPTION OF THE DRAWINGS

FIG. 1A-I. Optimization of pig heart slice biomimetic culture conditions. Once a full pig heart is obtained (A), the left ventricle is dissected into 1-2 cm³ cubes and placed on a holder with the epicardium facing down so the cutting occurs in alignment with the cardiac myofibril orientation (B). (C) Setup for slicing 300 μm thick heart slices in ice-cold bath using a vibrating microtome Model 7000smz-2 from Campden Instruments Ltd. (D) Example of the transwell culture setup using air-liquid interface. (E) Example of the heart slice trimmed and glued to light polyurethane supports and submerged in the medium in a 6-well plate, which is covered by the C-Dish cover containing graphite electrodes (F) and connected to the C-Pace EM stimulator from IonOptix Ltd (G). Quantification of heart slice viability overtime using MTT assay in either stimulated or unstimulated culture in standard medium (M199/ITS) (H) or optimized medium (I) (n=5 pig hearts each in triplicate, Two-Way ANOVA test was conducted to compare between groups; *$p<0.05$ compared to the unstimulated culture at the same time point, and #$p<0.05$ compared to fresh heart slices at day 0). Unstimulated: transwell culture, Unstimulated Glued: transwell culture with slices glued to the transwell.

DETAILED DESCRIPTION

Figures 2A, 2B, 2C:
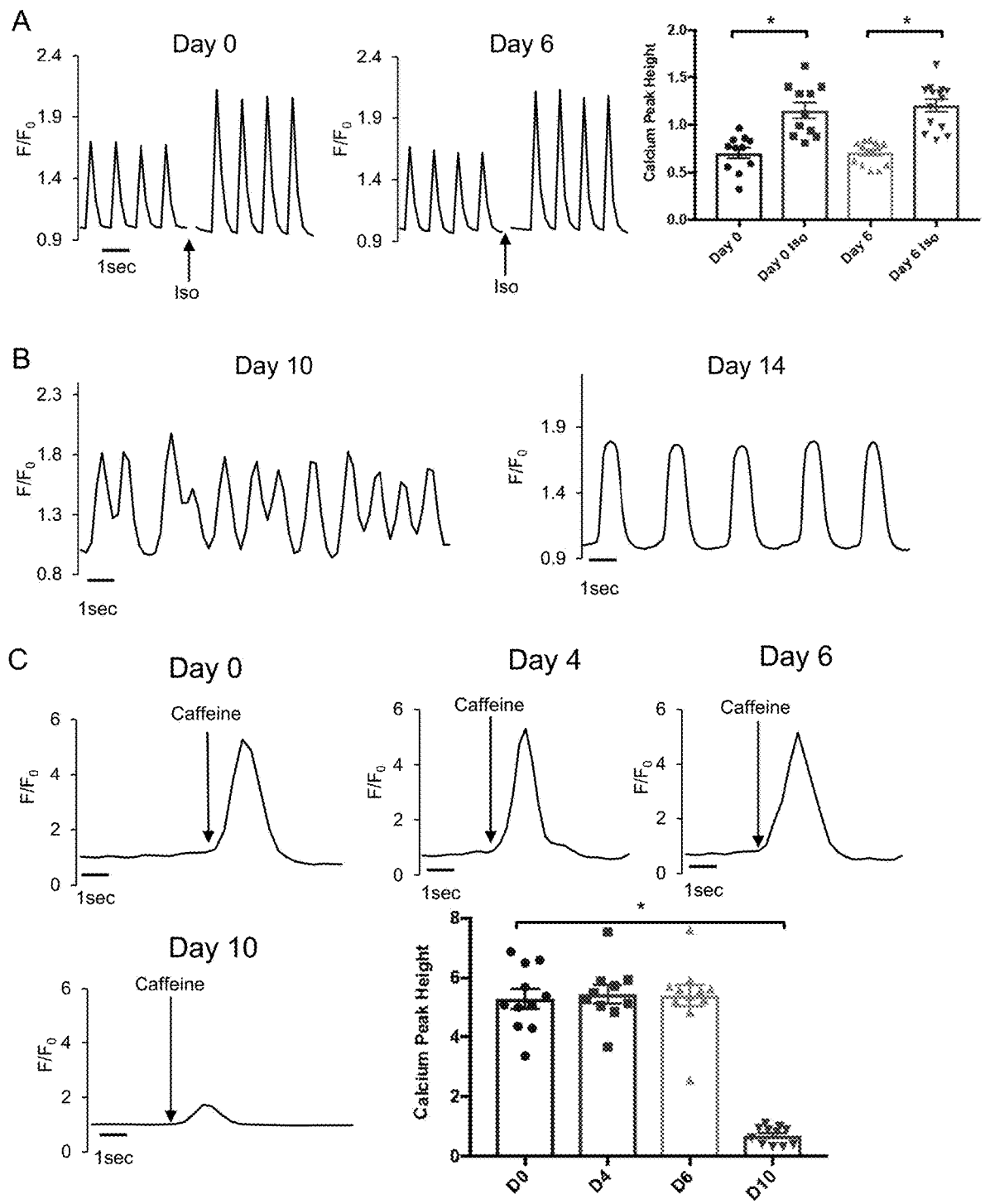
FIG. 2A-C. Calcium homeostasis in heart slices remains stable for 6 days in the biomimetic stimulated culture system. (A) Representative calcium signal trace from a fresh heart slice (Day 0) and after 6 days in culture (Day 6) with and without 1 μM isoproterenol (Iso) stimulation. Transients were recorded after loading the heart slices with Fluo-4 calcium dye and using 1 Hz/20 V electrical stimulation at the time of recording. Quantification of calcium signal amplitude with and without stimulation with isoproterenol shows a similar patterns of calcium transients at day 0 and day 6 in culture (n=4 pig hearts, 10-15 cells analyzed in each group, Two-Way ANOVA test was conducted to compare between groups; *$p<0.05$ comparing baseline to Iso stimulation at the same time point, p-value$_{D0\ vs\ D6}=0.95$, and p-value$_{D0\ Iso\ vs\ D6\ Iso}=0.93$). (B) Examples of irregular calcium transients from heart slices in culture for 10 (left) or 14 (right) days with no synchronization with electrical stimulation. (C) Representative traces and quantification of calcium amplitude following caffeine stimulation of heart slices as an indicator of the SR calcium contents in fresh heart slices (Day 0), 4, 6, and 10 days after culture (n=3 pig hearts each, 10-15 cells were analyzed from each group, One-Way ANOVA test was conducted to compare between groups; *$p<0.05$ compared to D0, p-value$_{D0\ vs\ D4}=0.97$, and p-value$_{D0\ vs\ D6}=0.95$).

Embodiments of the disclosure provide a reliable medium-throughput culture system for heart slices which may be used as a platform for testing the efficacy and cardiotoxicity of candidate therapeutics.

As used herein, the term "heart slice" or "heart organotypic slice" refers to a slice of heart which is obtainable from an isolated heart and retains the three-dimensional connectivity of the intact organ. The cell-cell interactions are preserved, and there is no selection of a particular cell type among the different cell types that constitute the organ. Several methods for obtaining heart organotypic slices are known to the skilled person and described in the art. Those include, for example, slicing using a vibratome, agarose embedding followed by sectioning by a microtome, or slicing using a heart matrix. The thickness of the heart organotypic slice may be comprised of 100 and 1000 µm, e.g. 100 and 500 µm. In some embodiments, the thickness of the heart organotypic slice is about 300 µm.

Typically, the heart organotypic slice according to the disclosure is obtainable from a mammal, such as a human, non-human primate, pig, cattle, horse, sheep, goat, rabbit, dog, cat, or rodent such as a rat, mouse, or guinea pig.

Embodiments of the disclosure provide a method for culturing heart tissue, comprising culturing a slice of the heart tissue in a culture medium, wherein the culture medium comprises fetal bovine serum (FBS), vascular endothelial cell growth factor (VEGF), and fibroblast growth factor (FGF; also known as FGF-basic); and simultaneously applying electrical stimulation to the slice while the heart slice is in culture.

Suitable culture medium includes any medium which provides the appropriate physicochemical environment to the slice and also minimally contains FBS, VEGF, and FGF. Such medium will normally contain nutrients, a buffer, and salts. In some embodiments, the basal medium is, for example, medium 199 (M199) which is then supplemented with various growth factors, serum, antibiotics etc. Other suitable basal media include, but are not limited to DMEM, RPMI1640, and HPSS among others. Suitable media are well known in the art and are commercially available from a variety of manufacturers, such as Gibco (Invitogen, France). In addition to FBS, VEGF, and FGF, the basal medium may also be supplemented with, e.g. insulin-transferrin-selenium (ITS) and an antibiotic-antimycotic solution (e.g. containing penicillin, streptomycin, and amphotericin B). In some embodiments, the culture medium does not include 2,3-butanedione monoxime (BDM). In some embodiments, the culture medium does not include any fatty acids added in addition to fatty acids present in the FBS.

In some embodiments, the culture medium is replaced, partially or totally, at regular intervals, for example every 3 days, every 2 days, every day, twice a day (e.g. every 12 hours), three times a day (e.g. every 8 hours), or more frequently. In some embodiments, the culture medium is oxygenated according to methods known in the art prior to being added to the culture. In the method according to the disclosure, the slices are cultured in standard tissue culture conditions. For example, the slices can be placed in an incubator, which provides an atmosphere containing 5% $CO_2$, and which maintains a temperature of about 37° C.

The method according to the invention enables the long-term in vitro culture of heart slices. In some embodiments, the heart slices are cultured for at least 2 days, e.g. at least 3, 4, 5, 6, 7, 8, 9, 10, 11, 12, 13, or 14, days or more. In some embodiments, the cultures are viable for more than 2 weeks, e..g more than 3, 4, or 5 weeks or more. The viability of the slice can be assessed by a variety of methods well known in the art, such as by measuring contractility and by assessing the cardiac structural architecture by immunohistochemistry.

Electrical stimulation may be applied to the heart slice using any known suitable apparatus or device that can be programmed to provide continuous electrical stimulation, such as the C-Pace stimulator (Ion-Optics Co., MA) which is able to accommodate eight 6-well plates at once. In some embodiments, the C-Dish (Ion-Optics Co., MA) is used in combination with the C-Pace. The C-Dish places carbon electrode elements in a variety of standard culture plates and a ribbon cable connector provides access to the field stimulating electrodes. In some embodiments, the C-Dish top and graphite electrodes are replaced at least once per day. Electrical stimulation allows for emulation of the cardiac milieu. In some embodiments, the electrical stimulation applied to the slice has a frequency of 0.5 to 2 HZ, e.g. about 0.6 HZ or about 1.2 HZ. In some embodiments, the electrical stimulation has a voltage of 5-15 V, e.g. about 10 V.

Applying a physiological mechanical load may be important for the maintenance of cardiac structural, functional and transcriptional properties. Thus, in some embodiments, the culture system provides simultaneous mechanical loading (e.g. 0-125 mmHg) and electrical stimulation. Methods of providing a mechanical load are known in the art. In some embodiments, to provide a mechanical load that does not require a complex bioengineered devices, and to enable heart slices to freely contract, the slices may be glued to small, light-weight polyurethane supports, e.g. using a HISTOACRYL® Blue topical skin adhesive.

Further embodiments of the disclosure provide methods for screening candidate therapeutic agents for therapeutic effect or cardiotoxicity using a culture system as described herein. In some embodiments, the method comprises contacting the slice being cultured with a candidate therapeutic agent and measuring one or more factors within the heart tissue that are indicative of the therapeutic effect or cardiotoxicity of the candidate drug. In some embodiments, the step of contacting comprises adding the candidate therapeutic agent to the culture medium. In some embodiments, the step of contacting comprises infecting the slice with a virus expressing the candidate therapeutic agent, e.g. to screen for potential gene therapies for disorders such as heart failure.

As used herein, the expression "screening therapeutic agents" includes screening drugs for modulating cardiac function, screening drugs for cardiac toxicity, etc. This can be performed both on healthy and on diseased heart slices. The type of cardiotoxicity may be, for example, cardiomyopathy (systolic or diastolic dysfunction), arrhythmia, myo-pericarditis, QT prolongation, increased heart rate, dromotropic changes, atrial fibrillation, vasospasm, cardiac arrest, and ischemia.

In some embodiments, the one or more factors indicative of the therapeutic effect or cardiotoxicity includes at least one of measuring cardiomyocyte proliferation, measuring transverse conduction velocity, determining viability of the heart tissue, measuring the contractility of the heart tissue, measuring calcium homeostasis, measuring calcium signal propagation, measuring electrophysical properties of single cardiomyocytes, measuring action potential, and measuring mitochondrial metabolism.

The viability of a heart slice may be determined using methods known in the art, e.g. by quantifying the activity of the mitochondrial NAD(P)H-dependent cellular oxidoreductase enzymes as a measure of metabolic activity using e.g. the MTT assay. Reduced viability may be indicative of cardiomyopathy and/or ischemia.

Contractility of the heart tissue may be assessed using methods known in the art, e.g. by evaluating force generation and speed of contraction and relaxation during electrical stimulation (e.g. at 1-1.2 Hz). Using a dual-mode lever allows both the force (contractility) and length of the heart slice to be measured and altered during the experiment. These measures may be an indicator for the functional deterioration in force production in the heart slice in a dose and time dependent manner. Reduced contractility may be indicative of systolic dysfunction.

Calcium homeostasis and calcium signal propagation may be assessed throughout the tissue using methods known in the art, e.g. using a calcium sensitive dye and line-scan confocal microscopy. Irregular calcium homeostasis may be indicative of arrhythmia Single cardiomyocytes may be isolated from the heart slices using methods known in the art and the cellular electrical function may be recorded from the whole cell configuration, e.g. using the patch-clamp technique. $I_{Ca,L}$, $I_{Na}$, or K+-currents may be assessed. Conduction slowing may prompt evaluation of $I_{Na}$, whereas QT prolongation may necessitate evaluation of late $I_{Na}$, $I_{Ca,L}$ and Kv currents. Disruption in electrophysiology may be indicative of arrhythmia.

In some embodiments, the action potential and calcium homeostasis may be assessed simultaneously using multi-parametric optical mapping in cardiac slices by combining transmembrane potential (Vm) sensitive dye and cytosolic calcium (Ca) sensitive dye. Using optical AP and calcium transient (CaT) recordings, restitution properties (waveform duration versus stimulation cycle length) may be measured. These measurements may be conducted in the presence or absence of beta-adrenergic stimulation to ensure that the effects of the potential cardiotoxins on action potential and calcium are not shifted due to the catecholamine presence in vivo.

The integrity of mitochondrial metabolism and the ability to produce ATP through oxidative phosphorylation is essential for cardiomyocyte integrity and performance. Therefore, the effect of potential cardiotoxins on mitochondrial metabolism may be assessed using methods known in the art, e.g. by measuring the oxygen consumption rate and extracellular acidification rate of intact human heart slices, e.g. using a Seahorse XF24 analyzer (Seahorse Bioscience, Billerica, Mass.). A metabolic flux disturbance may be indicative of early signs of systolic dysfunction and/or arrhythmia Any drug candidate for the treatment of any disease or disorder, including anti-cancer therapies, may be tested for efficacy or cardiotoxicity using the model system described herein. The types of drugs that may be tested are varied and include, for example, anthracyclines, antibodies, kinase inhibitors, serotonin agonists, Cox2 inhibitors, cannabinoids, nitrogen mustards, and sympathomimetics, among others.

The culture system described herein may be used for any research application related to heart tissue. For example, the culture system described herein may be used to study the mechanism of target proteins in human heart tissues. The culture system may also be used for disease modeling wherein human heart tissue is obtained from a diseased patient. This will allow for the study of the mechanism of disease and to screen for specific therapies of the disease.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE 1

Summary

Preclinical testing of cardiotoxicity and efficacy of novel heart failure therapies faces a major limitation: the lack of an in situ culture system that emulates the complexity of human heart tissue and maintains viability and functionality for a prolonged time. The objective of this study was to develop a reliable, easily reproducible, medium-throughput method to culture heart slices under physiological conditions for a prolonged period of time. Here, we describe a novel, medium-throughput biomimetic culture system that maintains viability and functionality of human and pig heart slices (300 μm thickness) for 6 days in culture. We optimized the medium and culture conditions with continuous electrical stimulation at 1.2 Hz and oxygenation of the medium. Functional viability of these slices over 6 days was confirmed by assessing their calcium homeostasis, twitch force generation, and response to β-adrenergic stimulation. Temporal transcriptome analysis using RNAseq at day 2, 6, and 10 in culture confirmed overall maintenance of normal gene expression for up to 6 days, while over 500 transcripts were differentially regulated after 10 days. Electron microscopy demonstrated intact mitochondria and Z-disc ultra-structures after 6 days in culture under our optimized conditions. This biomimetic culture system was successful in keeping human heart slices completely viable and functionally and structurally intact for 6 days in culture. We also used this system to demonstrate the effects of a novel gene therapy approach in human heart slices. Furthermore, this culture system enabled the assessment of contraction and relaxation kinetics on isolated single myofibrils from heart slices after culture.

Methods

Heart Tissue Collection From Pigs and Humans

To collect hearts from the 15 pigs used in the current study, all animal procedures were in accordance with the institutional guidelines of Tenaya Therapeutics and the University of Louisville and approved Institutional Animal Care and Use Committee at both places. Fresh human hearts were provided from consented donors through the Maryland Legacy Foundation (Novabiosis) and all procedures were approved by the Institutional Review Board of the University of Louisville. In this study, we used 3 de-identified human hearts from donors aged 36, 42, and 45 years old with no cardiovascular disease history. As described before in [11-15], pig or human hearts were clamped at the aortic arch and perfused with 1 L sterile cardioplegia solution (110 mM NaCl, 1.2 mM $CaCl_2$, 16 mM KCl, 16 mM $MgCl_2$, 10 mM $NaHCO_3$, 5 units/ml heparin, pH to 7.4), then the hearts were preserved on ice-cold cardioplegic solution until transported to the lab on wet ice within 12 hours.

Heart Slicing

Hearts were placed in a sterile glass container with cardioplegia solution and then the left ventricle was cut into 1-2 $cm^3$ blocks. Each heart tissue cube was placed on a 4% agar bed on top of the specimen holder with the epicardium glued to the agar bed using Histoacryl Blue tissue glue and the endocardium facing up. The tissue block holder was placed on the cutting chamber of a Vibrating Microtome 700SMZ (Campden Instruments). The cutting chamber was filled with cold (4° C.) oxygenated modified Tyrode's solution (Tyrode's cutting solution, NaCl 140 mM; KCl 6 mM; glucose 10 mM; HEPES 10 mM; $MgCl_2$ 1 mM; $CaCl_2$ 1.8 mM; 2,3-butanedione monoxime (BDM) 10 mM; pH 7.4). To limit cardiomyocyte damage while slicing, the vibrating microtome's z-axis vibration was calibrated with the ceramic cutting blade to <0.5 μm. Prior to slicing the vibrating microtome was pre-set to 300 μm slice thickness, 0.03 mm/s advance speed, and 80 Hz vibration frequency at 2 mm horizontal vibration amplitude. Following slicing, each slice was transferred immediately to 100 μm nylon mesh cell strainers immersed in oxygenated washout Tyrode's solution at room temperature (NaCl 140 mM; KCl 4.5 mM; glucose 10 mM; HEPES 10 mM; $MgCl_2$ 1 mM; $CaCl_2$ 1.8 mM; 2× Antibiotic-Antimycotic; pH 7.4) and a metal washer was placed on the top of the slice to prevent wrinkling. The heart slices were kept in the Tyrode's washing solution for at least 20 minutes to wash out the BDM and warm the tissue to room temperature.

Heart Slice Culture

For unstimulated transwell culture, slices were cultured at a liquid-air interface using porous transwell inserts (PICMORGO, Millipore, USA) in 6 well plate format. Slices were provided with 1 ml medium composed of Medium 199 (Thermo Scientific), 2% Penicillin-Streptomycin (Thermo Scientific), 1× ITS (Insulin, Transferrin, Selenium (Thermo Scientific)), and 10 mM BDM. The slices were placed in a 37° C. incubator with humidified air with 5% CO2 and the culture medium was changed daily.

For stimulated culture, slices were glued at each end into sterilized polyurethane printer 6 mm wide printer timing belt with metal wires embedded (Uxcell) using histoacryl blue tissue glue. Then the supported heart slices were transferred into 6 well plates containing 6 ml of medium in each well (Medium 199, 1× ITS Supplement, 10% FBS, 5 ng/ml VEGF, 10 ng/ml FGF-basic, and 2× Antibiotic-Antimycotic). Then a C-Dish top with graphite electrodes (Ionoptix) was placed on the top of the 6 well plate and connected to the C-Pace-EM system (Ionoptix), and stimulated at 10V, 1.2 Hz. The plates were placed in the incubator at 37° C. with humidified air and 5% $CO_2$. Media was changed three times/day with preoxygenated media. The C-Dish top with the graphite electrodes was replaced every day to avoid release of toxic carbon into the medium.

Calcium-Transient Assessment

Heart slices were loaded with Fluo-4 for 30 min at room temperature before being transferred to the superfusion chamber. The loading solution contained a 1:10 mixture of 5 mM Fluo-4 AM in dry DMSO and Powerload™ concentrate (Invitrogen), which was diluted 100-fold into extracellular Tyrode's solution (NaCl 140 mM; KCl 4.5 mM; glucose 10 mM; HEPES 10 mM; $MgCl_2$ 1 mM; $CaCl_2$ 1.8 mM; 2× Antibiotic-Antimycotic; pH 7.4). An additional 20 minutes was allowed for de-esterification before recordings were taken. Contractions and calcium transients were evoked by applying voltage pulses at 1 Hz between platinum wires placed on either side of the heart slice and connected to a field stimulator (IonOptix, Myopacer). Fluo-4 fluorescence transients were recorded via a standard filter set (#49011 ET, Chroma Technology). Resting fluorescence was recorded after cessation of pacing, and background light was obtained after removing the heart slice from the field of view at the end of the experiment. All analyses of calcium transients were based on calcium transients recorded from single cardiomyocytes within the heart slice and the calcium transient amplitude was assessed as the average of 10 consecutive beats for each cardiomyocyte. For β-adrenergic stimulation we used 1 μM isoproterenol and for SR calcium release we used 10 mM caffeine. Caffeine stimulation caused major movement of the slice, therefore, for the caffeine experiments, the slices were glued to the coverslip and they were preincubated with 10 mM BDM to prevent movement.

Contractile Force Assessment

For contractile force measurement, middle strips of the heart slice were assessed using the Dual-Mode Muscle Lever System (300C-LR, Aurora Scientific Inc, Aurora, Canada). The heart slice strip was kept in Krebs Ringer solution gassed with a mixture of 95% $O_2$ and 5% $CO_2$ throughout the procedure. The heart slice was tied to a metal pin from one end, and the other end was attached to the force transducer with 4-0 silk suture. The heart slice was positioned between two platinum electrodes to provide electrical stimulation using 701C stimulator (Aurora Scientific Inc.). To find optimal length for isometric contraction, the heart slice strip was slowly stretched until passive force was ~30 mN. The preparation was then warmed to 37° C., allowing 10 min for thermo-equilibration, before measurements of contractile properties. We measured isometric specific twitch force at 1 Hz at tetanic electrical stimulations (150 Hz, 800-1000 mA, 0.25 ms pulse). The contractile properties of the same heart slice were assessed basally or after addition of 1 μM isoproterenol in the myobath to evaluate the inotropic response of the heart slice to b-adrenergic stimulation. All data were recorded and analyzed using commercial software (DMCv5.5 and DMAv5.3, Aurora Scientific). Force was normalized to cross-sectional area (mN/$cm^2$); to estimate the heart slice cross sectional area, heart slice strip weight (g) was divided by the slice length (cm) multiplied by the muscle density (1.06 g/cm3).

MTT Viability Assay

For the MTT assay we used the Vybrant® MTT Cell Proliferation Assay Kit (Thermo Scientific) according to the manufacturer's protocol with some modifications. Briefly, using a sterile scalpel, we cut 0.2-0.5 $cm^2$ segments of the heart slice to perform the MTT assay. These pieces were each placed in a well of 12 well plate containing 0.9 ml of growth media with 0.1 ml of the reconstituted MTT substrate according to the manufacturer's protocol. The tissues were incubated for 3 hours at 37° C. and viable tissue metabolized the MTT substrate creating a purple color formazan compound. To extract the purple formazan from the heart slices, we transferred the tissue into 1 ml of DMSO and incubated it at 37° C. for 15 minutes, or until the tissue was translucent and no longer dark purple. The intensity of the purple color was measured using a Cytation plate reader (BioTek) at 570 nm. The readings were normalized to the weight of each heart slice and converted into OD/mg tissue. In addition, to avoid any possible signal saturation, for each sample we perform reading for 1:2, 1:5 and 1:10 dilution of the MTT product and take the average of all readings normalized to its dilution factor.

Heart Slice Fixation, Mounting and Immunofluorescence

Heart slices were fixed in 4% paraformaldehyde for 24 hours. Fixed tissue underwent dehydration in 30% sucrose overnight and was then embedded in optimal cutting temperature compound (OCT compound) and gradually frozen in isopentane/dry ice bath. OCT embedded blocks were stored at −80° C. until sectioning. 8 μm sections were cut and immunostained for target proteins using the following modified procedure: To remove the OCT compound the slides were heated for 3-5 minutes at 95° C. until the OCT compound melted. Then 1-2 ml of PBS were added to each slide and incubated at room temperature for 10-30 minutes until the OCT compound washed off. Sections were then permeabilized by incubating them for 30 minutes with 0.1% Triton-X in PBS at room temperature. Then the Triton-X was washed with PBS and non-specific antibody binding in the sections was blocked by 3% BSA solution for 1 hour at room temperature. After washing BSA with PBS, the primary antibodies (1:100 dilution in 1% BSA) Connexin 43 (Abcam; #AB11370), Troponin-T (Thermo Scientific; #MA5-12960), alpha-actinin (Sigma-Millipore; #A7732), and Phospho-Histone H3 (Abcam, #AB5176)) were added to the section for 90 minutes followed by the secondary antibodies (1:200 dilution in 1% BSA) Anti-mouse Alexa Fluor® 594 (Thermo Scientific; #T-862), Anti-mouse Alexa Fluor® 488 (Thermo Scientific; #A16079), Anti-rabbit Alexa Fluor® 594 (Thermo Scientific; #T6391) for another 90 minutes separated by 3 washes with PBS. To distinguish the bonafide target staining from background, we used a secondary antibody only as a control. Finally, the DAPI stain was added and the slides were mounted in vectashield (Vector Laboratories) and sealed with nailpolish. All immunofluorescence imaging and quantification was performed using a Cytation 1 high content imager and the fluorescent signal quantification and masking was performed using the Gen5 software.

Electron Microscopy

Heart slices were fixed for 48 hours in a fixative reagent (2% glutaraldehyde and 2% paraformaldehyde in 0.1 M phosphate buffer (pH 7.4). Fixed slices were then treated with 1% osmium tetroxide for 2 hours for further fixation. Heart slices were then dehydrated by incubating in successively increasing concentrations of ethanol (50, 70, 95 and 100%) each for 15 minutes. Then the heart slices were embedded in epoxy embedding resin (Sigma Millipore). The blocks of heart slices were cut using Leica® model EMUC7 ultra microtome and placed onto copper grids. For improved visualization, the tissue grids were stained with uranyl acetate and lead citrate. The stained grids were examined using a Hitachi® HT7700 Model Transmission Electron Microscope.

RNAseq Analysis

RNA from heart slices were isolated using the Qiagen®, miRNeasy® Micro Kit, #210874, following homogenization of the tissue in QIAzol® (Qiagen). Using the Ovation RNA-seq System v2 Kit (NuGEN), total RNA (20-50 ng) was reverse transcribed to synthesize first-strand cDNA using a combination of random hexamers and a poly-T chimeric primer. The RNA template was then partially degraded by heating and the second-strand cDNA was synthesized using DNA polymerase. Double-stranded DNA was then amplified using single primer isothermal amplification (SPIA). Random hexamers were then used to linearly amplify the second-strand cDNA. cDNA samples were fragmented to an average size of 200 bp using the Covaris® S2 sonicator. Libraries were made from the fragmented cDNA using the Ovation® Ultralow V2 kit (NuGen).

Following end repair and ligation, the libraries were PCR amplified with 9 cycles. Library quality was assessed by a Bioanalyzer on High-Sensitivity DNA chips (Agilent) and concentration was quantified by qPCR (KAPA)[3,4]. The libraries were sequenced on a HiSeq® 2500 sequencer with a single-read, 50-cycle sequencing run (Illumina®). We utilized the RNAseq-analysis pipeline reported previously[4]. Known adapters and low-quality regions of reads were trimmed using Fastq-mcf (code.google.com/p/ea-utils). Sample QC was assessed using FastQC (bioinformatics.babraham.ac.uk/projects/fastqc/). Reads were aligned to the pig-reference assembly Sscrofa11.1 using Tophat 2.0.13. Gene expression was tallied by Subread featureCounts 7 using Ensembl's gene annotation for Sscrofa11.1. Finally, we calculated differential expression P-values using edgeR 8. Here, we first filtered out any genes without at least two samples with a CPM (counts per million) between 0.5 and 5000. CPMs below 0.5 indicates nondetectable gene expression, and CPMs above 5000 are typically only seen in mitochondrial genes. If these high-expression genes were not excluded, their counts would disproportionately affect the normalization. After excluding these genes, we renormalized the remaining ones using "calcNormFactors" in edgeR, then calculated P-values for each gene with differential expression between samples using edgeR's assumed negative-binomial distribution of gene expression. We calculated the false discovery rates (FDRs) for each P-value with the Benjamini-Hochberg method 9 based on the built-in R function "p.adjust".

Metabolic Flux Assessment

The bioenergetics of intact heart slices were measured using a Seahorse Bioscience XF24 Flux Analyzer. For these experiments, the treatment medium was replaced with 675 µl of assay medium: unbuffered DMEM supplemented with 5.5 mM glucose, 0.5 mM glutamine and 1 mM pyruvate, 1 mM carnitine, 0.6 mM acetate. The pH of the assay medium was adjusted to 7.4 with NaOH. Following microplate insertion, the XF24 automated protocol consisted of a 12 min delay followed by baseline oxygen consumption rate (OCR) and extracellular acidification rate (ECAR) measurements [3×(3 min mixing, 2 min wait and 3 min measure)]. All experiments were conducted at 37° C. Data were normalized to the protein contents of the heart slices.

Glucose Utilization Assay

To assess glucose utilization, we measured the tritiated water produced from [5-$^3$H]-glucose during a 4-hour incubation with the heart slices. Briefly, heart slices were incubated in culture medium containing 2 µCi/ml [5-$^3$H]-glucose (Moravek Biochemicals, Brea, Calif., USA). Following incubation for 4 hours, 100 µl of media was collected and added to 100 µl of 0.6 N HCl in a microcentrifuge tube. This tube, with the tube cap removed, was placed in a scintillation vial containing 500 µl of dH$_2$O to allow for evaporation diffusion of [$^3$H]$_2$O. After incubation at 37° C. for 72 hours, the microcentrifuge tube was removed from the vial, 10 ml of scintillation fluid was added, and scintillation counting was performed using a Tri-Carb® 2900TR Liquid Scintillation Analyzer (Packard Bioscience Company, Meriden, Conn., USA). Glucose utilization was then calculated, with considerations for the specific activity of [5-$^3$H]-glucose, incomplete equilibration and background, dilution of [5-$^3$H]- to unlabeled-glucose, and scintillation counter efficiency. Data were normalized to the protein contents of each heart slice.

Single Myofibril Isolation and Contractile Mechanics Assessment

Myofibril mechanics were quantified using the fast solution switching technique. Frozen porcine LV slices were skinned in 0.5% Triton-X in rigor solution (132 mM NaCl, 5 mM KCl, 1 mM MgCl$_2$, 10 mM Tris, 5 mM EGTA, pH 7.1) containing protease inhibitors (10 µm leupeptin, 5 µm pepstatin, 200 µm PMSF and 10 µm E64), as well as 500 µm NaN$_3$ and 500 µm DTT at 4° C. overnight. Skinned LVs were washed in fresh rigor solution and homogenized (Tissue-Tearor, Thomas Scientific) in relaxing solution (pCa 9.0) containing protease inhibitors. Myofibril suspensions were transferred to a temperature-controlled chamber (15° C.) containing relaxing solution. Myofibril bundles were mounted between two micro-tools. One tool was connected to a motor that could produce rapid length changes (Mad City Labs). The second tool was a calibrated cantilevered force probe (7-10 µm/µN; frequency response 2-5 KHz). Myofibrils were set 5-10% above slack myofibril length. Average sarcomere lengths and myofibril diameters were measured using ImageJ software. Mounted myofibrils were activated and relaxed by rapidly translating the interface between two flowing streams of solutions of pCa 9.0 and pCa 4.5. Data were collected and analyzed using customized LabView software. Measured mechanical and kinetic parameters were defined as follows: resting tension (mN/mm$^2$)=myofibril basal tension in fully relaxing condition; maximal tension (mN/mm$^2$)=maximal tension generated at full calcium activation (pCa 4.5); the rate constant of tension development following maximal calcium activation=$k_{ACT}$; and relaxation parameters were defined as: duration of the linear relaxation=linear duration, and the rate constant of exponential relaxation=fast $k_{REL}$.

Statistical Analyses

For all assays, power analyses were performed to choose the group sizes which will provide >80% power to detect a 10% absolute change in the parameter with a 5% Type I error rate. These power analyses indicated a minimum of 4 experimental replicates per group, therefore, we used a range of 5-15 experimental replicates per group for each assay. Then, Kolmogorov-Smirnov (K-S) test for normality was conducted; all data sets showed normal distribution. Then, differences between 2 groups were examined for statistical significance with unpaired Student t tests. However, to compare data consisting of more than 2 groups, we performed one- or Two- way ANOVA tests followed by Bonferroni post hoc multiple comparisons to get the corrected p-value. A value of P<0.05 was regarded as significant. Error bars indicate SEM. The person who performed the analysis was blinded to the experimental groups.

Results

Development and Optimization of a Biomimetic Culture System for Porcine Heart Slices Previous reports have shown that culture systems using an air-liquid interface and M199/ITS media (FIG. 1A-D) did not maintain heart slice functionality for more than 24 hours[9-12]. Therefore, we tested the effect of mimicking the biological conditions in the heart. First, we provided continuous electrical stimulation to pig heart slices at the physiological rate (1.2 Hz) (FIG. 1E-G). To provide adequate oxygen supply to the slices, the medium was changed every 8 hours with oxygenated medium. It has recently been shown that applying a physiological mechanical load is essential for the maintenance of cardiac structural, functional and transcriptional properties[15]. To provide minimal mechanical load that does not require the complex bioengineered devices, and to enable heart slices to freely contract, we glued the slices to small, light-weight polyurethane supports using a Histoacryl Blue topical skin adhesive (FIG. 1E). Given that cardiomyocytes are metabolically active, we used the MTT assay to quantify the activity of the mitochondrial NAD(P)H-dependent cellular oxidoreductase enzymes, as a measure of metabolic activity to assess heart slice viability. First, we optimized the MTT assay for the tissue slices to avoid signal saturation. Using the MTT assay, we found that electrical stimulation alone did not extend the viability of the heart slices (FIG. 1H), but instead decreased viability when applied to slices cultured in the media formulation commonly used for heart slices; Medium 199, ITS, and antibiotics[10-12, 14]. We reasoned that medium optimization may be required to support the metabolic needs of active cardiac tissue. To address this potential need, we tested the addition of several components known to support the culture of human iPSC-CMs and induced cardiomyocytes derived from direct cardiac reprogramming[17-19]. These components were; FBS, FGF/VEGF, fatty acids (oleic and palmitic acids), and the basal medium, RPMI/B27[18]. We first implemented these different components and their combinations in the unstimulated transwell culture system and assessed how long each combination could support the viability of porcine heart slices. In this condition, the optimal formulation contained M199 as basal medium, 1× ITS, 10% FBS, and FGF/VEGF which showed significantly higher viability than any other media formulation at day 2 and 3. Next, we tested this new medium formulation in combination with the continuous electrical stimulation at different frequencies (0.6 Hz and 1.2 Hz). The new medium formulation, in conjunction with the continuous electrical stimulation at either frequency, maintained viable heart slices until day 6, after which viability declined progressively as assessed by MTT assay (FIG. 1I). Because 6 days of viable heart slice culture is adequate to support testing of efficacy or acute toxicity of most therapeutic agents, we considered this to be our baseline protocol and refer to this heart slice culture technique as the biomimetic stimulated culture system.

Functional Assessment of Pig Heart Slices

The major functional characteristic of heart tissue is contraction, which is preceded by induction of calcium transients upon electrical stimulation. To test these functions in heart slices cultured in our biomimetic stimulated culture system, we first assessed the induction of calcium transients over time. We observed that, within the first 6 days of culture in the biomimetic stimulated culture system, the slices perform similarly to fresh heart slices in that they did not exhibit any spontaneous calcium transients except upon electrical stimulation. In addition, on day 6 the heart slices responded to isoproterenol stimulation in a manner similar to fresh heart slices (FIG. 2A). Due to the slight beat-to-beat variation in calcium amplitude within the cell calcium recording, we performed the analysis on the average of 10 consecutive beats from each cell. However, by day 7, some cardiomyocytes showed spontaneous calcium transients. Nevertheless, the rest of the tissue still responded to electrical stimulation. This phenomenon of spontaneous calcium transients propagates quickly and included the entire heart slice on days 10 and 14 (FIG. 2B). The timing of this change aligns with the MTT viability data and reflects a variation in functional characteristics of the heart slice at this time point. Next, we assessed the calcium content of the sarcoplasmic reticulum (SR) following caffeine stimulation to release SR calcium stores. The SR calcium reserves during the first 6 days of culture were similar to those of fresh heart slices. However, there was a significant reduction in SR calcium content on day 10 in culture (FIG. 2C).

Figure 3A:
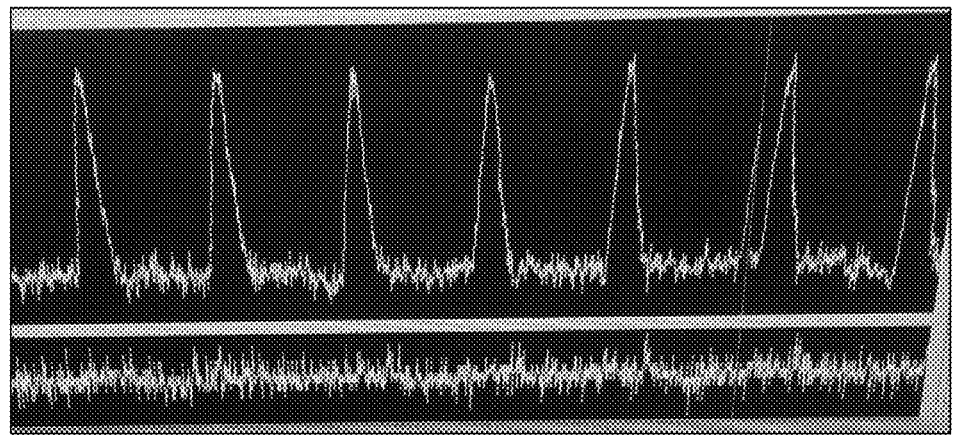
FIG. 3A-B. Contractile force generated by heart slices after 6 days in culture is comparable to fresh heart slices. (A) Contractile force assessment setup; the heart slice is hung between a force transducer (FT) and a stable post (P) between two electric electrodes (EE) for electrical stimulation. Upon stimulation, the slice contracts and the contraction is recorded using the designated software. (B) Bar graphs show the quantification of contractile force parameters in the presence or absence of isoproterenol (Iso) generated by fresh heart slices (Day 0) and after 6 days in culture (n=4 pig hearts each in triplicate, Two-Way ANOVA test was conducted to compare between groups; *$p<0.05$ comparing baseline to Iso stimulation at the same time point, twitch force: p-value$_{D0\ vs\ D6}=0.96$, p-value$_{D0\ Iso\ vs\ D6\ Iso}=0.81$; Time to 50% relaxation: p-value$_{D0\ vs\ D6}=0.47$, p-value$_{D0\ Iso\ vs\ D6\ Iso\ vs\ D6\ Iso}=0.43$; time to 100% relaxation: p-value$_{D0\ vs\ D6}=0.91$, p-value$_{D0\ Iso\ vs\ D6\ Iso}=0.36$).
Figure 3B:
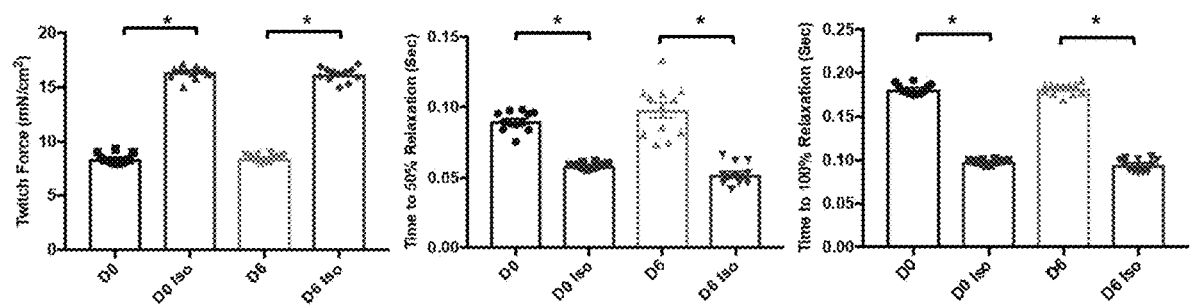

Finally, we assessed the ability of the heart slices to generate contractile force before and after culture using an Aurora Scientific Isolated Muscle System (FIG. 3A). Until 6 days in the biomimetic stimulated culture system, the heart slices produced contractile force similar to that of fresh slices and showed normal inotropic response to isoproterenol treatment (FIG. 3B). By day 10, contractile force was no longer detected in any heart slice.

Figure 4A:
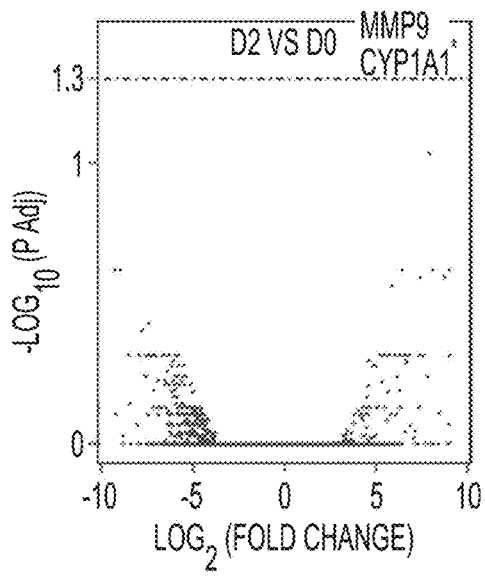
FIG. 4A-D. Temporal transcriptome analysis of heart slices shows no significant changes in gene expression for up to day 6 in culture. Volcano plots show significant changes in gene expression in heart slices. Fresh heart slices (D0) are compared to 2 days (A), 6 days (B) and 10 days (C) in our stimulated biomimetic culture. (D) Heat map showing log2 fold change in gene expression of representative cardiac, metabolic and fibroblast genes on days 2, 6, and 10 in culture compared to fresh heart slices (n=3 biological replicates from 3 different pig hearts).
Figure 4B:
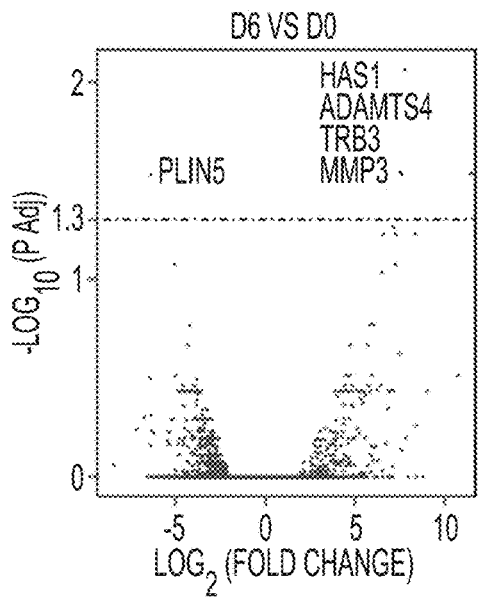
Figure 4C:
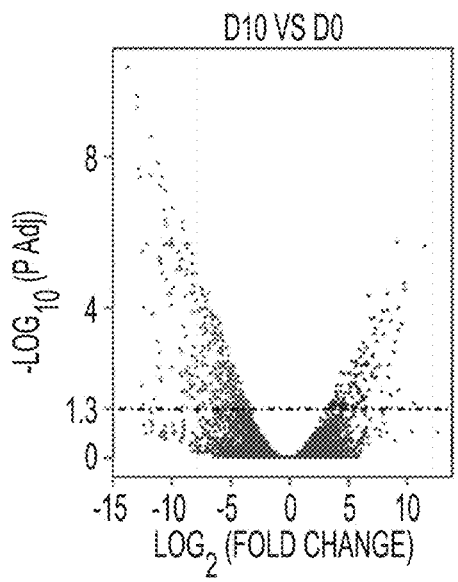
Figure 4D:
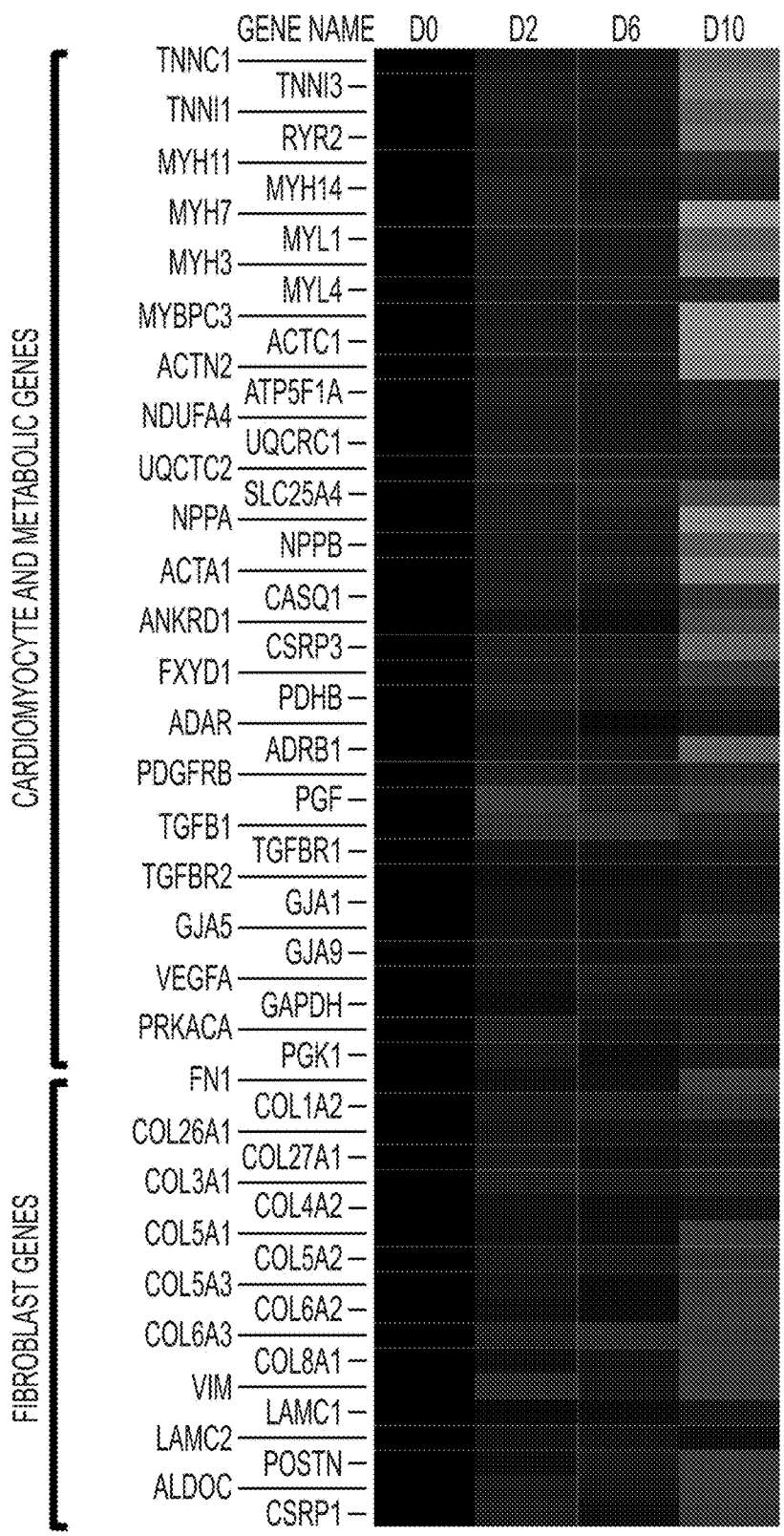
Figure 5A:
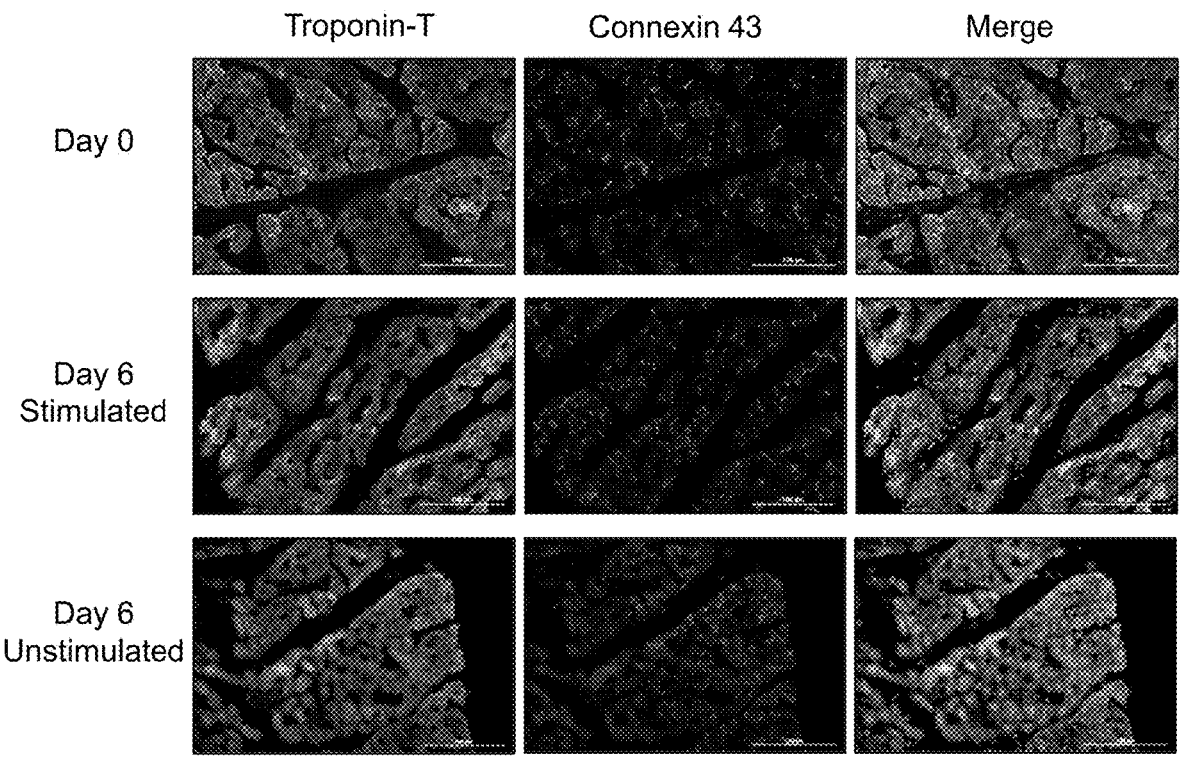
FIG. 5A-C. Biomimetic stimulated culture maintains the connexin 43 and myofilament ultrastructure for 6 days compared to unstimulated culture. (A) Representative immunofluorescence images showing expression of connexin 43 (red) in cardiomyocytes (green) in cross sections from either fresh heart slices (top panel), slices cultured for 6 days under biomimetic stimulated culture conditions (middle panel), or slices cultured for 6 days under unstimulated transwell conditions (bottom panel), (scale bar, 100 μm). (B) Quantification of the area occupied by connexin 43 in fresh heart slices compared to heart slices cultured for 6 days either under biomimetic stimulated culture or unstimulated culture (n=4 pigs, 3 replicates of each, One-Way ANOVA test was conducted to compare between groups; *$p<0.05$ compared to stimulated day 6 group, p-value$_{day\ 0\ vs\ stimulated\ day\ 6}=0.65$). (C) Electron microscopy images from stimulated culture (top panel) and unstimulated culture (bottom panel) for 6 days, show that the mitochondrial and Z-disc alignment and structure in biomimetic stimulated culture are not evident in unstimulated culture.
Figure 5B:
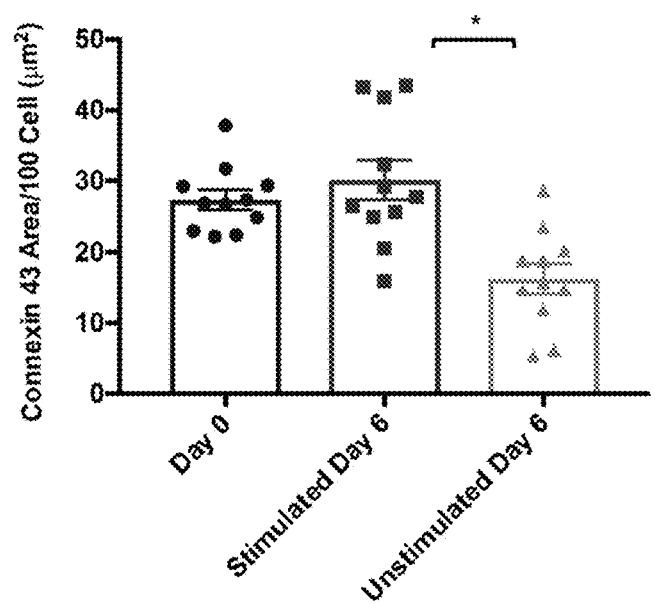
Figure 5C:
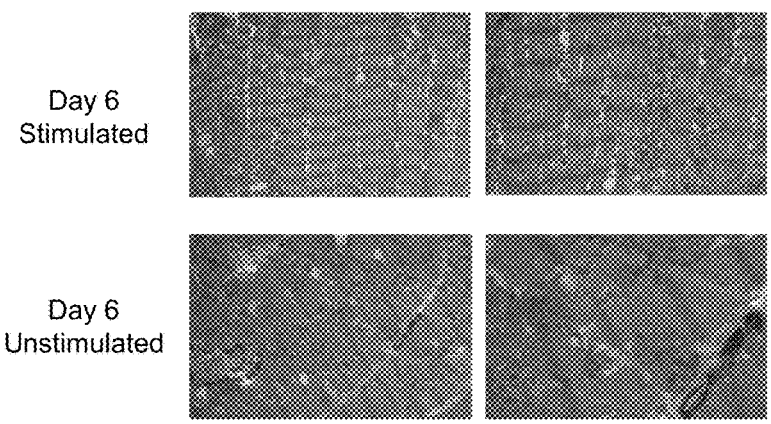

Transcriptome and Metabolic Profiling of Pig Heart Slices Under Optimized Conditions To assess changes in gene expression during culture, we performed a full transcriptome analysis of the heart slices before culture and compared these data to those of slices cultured in the biomimetic stimulated culture system for 2, 6, and 10 days. Only 2 and 5 transcripts were significantly differentially expressed after 2 and 6 days, respectively (FIG. 4 A&B). However, after 10 days in culture, there were significant changes in the expression of over 500 transcripts (FIG. 4C). The gene ontology (GO) terms of the genes downregulated after 10 days in culture were related to cardiac muscle, while the GO terms representing the upregulated genes focused on fibroblasts, extracellular matrix, and inflammation. These GO terms are indicative of the deterioration of myocyte health by day 10 in culture and the overrepresentation of fibroblasts and inflammatory cells. Furthermore, a heatmap of the expression of cardiac and fibroblast genes shows that downregulation of cardiac gene expression and upregulation of fibroblast gene expression are evident at day 10, but not before (FIG. 4D). A few exceptional genes were upregulated as early as day 2 (e.g. PDGFRB, PGF, TGFB1), which is likely a response to the presence of FGF and VEGF in the culture medium. Connexin 43 is the major conductance protein in the heart localized at gap junctions between cardiomyocytes to propagate the electrical signal through cardiac tissue. We found that over the first 6 days of culture in the biomimetic stimulated culture system, connexin 43 expression remained intact at the gap junctions and is similar to that in fresh heart slices. However, unstimulated transwell culture for 6 days resulted in distortion of the connexin 43 expression at the gap junction (FIGS. 5A and B). Furthermore, electron microscopy showed that mitochondrial and Z-disc alignment and structure remained intact for 6 days in the biomimetic stimulated culture system but was completely distorted in unstimulated cultures (FIG. 5C). Furthermore, the biomimetic stimulated culture was suitable for culturing pig heart slices from the border zone of infarcted hearts. The slice viability and connexin 43 expression was maintained for 6 days, just as we observed with slices from the healthy myocardium. The one early change noticed in our biomimetic stimulated culture system was a shift towards energetic reliance on glycolysis. As early as day 2 in culture, the heart slices utilized significantly less oxygen, yet maintained glycolytic activity. By day 8 however, oxygen utilization was nearly undetectable and glucose catabolism was significantly diminished. These interesting findings raised the question of how each component of the medium contributes to the metabolic state of the heart slice and whether the addition of fatty acids would improve the metabolic health of the myocardial slice. Therefore, we tested 4 different media formulations; M1: M199/ITS, M2: M199/ITS/FBS, M3: M199/ITS/FBS/VEGF/FGF, and M4: M199/ITS/FBS/VEGF/FGF/Fatty acids. Only heart slices cultured with M3 maintained full viability over 6 days and the addition of fatty acids deteriorated viability as assessed by MTT assay. Interestingly, we found that the addition of fatty acids to the culture medium significantly reduced connexin 43 expression, likely due to their mild solubilization effects on membrane proteins[20]. By assessing the metabolic flux in these heart slices over time, we found that M3 was the only medium that maintained the glycolytic capacity of the slices up to day 6, which is likely to be the reason underlying their more prolonged viability. Collectively, these data suggest that VEGF and FGF in heart slice medium maintains glycolytic capacity and that the addition of fatty acids does not improve heart slice function or viability.

Figure 6A:
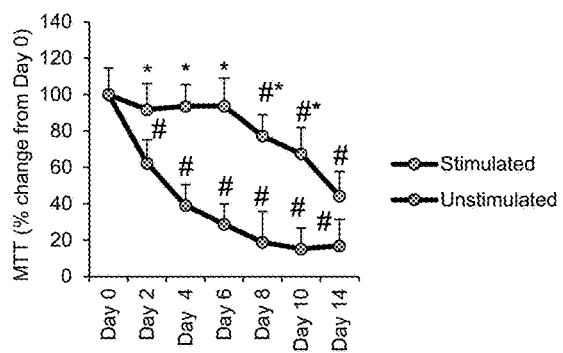
FIG. 6A-D. Human heart slices are functionally viable for 6 days in biomimetic stimulated culture. (A) Quantification of heart slice viability over time using MTT assay in either stimulated or unstimulated culture system in optimized medium (n=3 human hearts each in triplicate, Two-Way ANOVA test was conducted to compare between groups; *$p<0.05$ compared to the unstimulated culture at the same time point, and #$p<0.05$ compared to fresh heart slices at day 0). (B) Bar graph shows the quantification of the contractile force in the presence or absence of isoproterenol (Iso) generated by fresh human heart slices (Day 0) and after 6 days in biomimetic culture (n=2 human hearts each in triplicate, Two-Way ANOVA test was conducted to compare between groups; *$p<0.05$ comparing baseline to Iso stimulation at the same time point, twitch force: p-value$_{D0\ vs\ D6}=0.39$, p-value$_{D0\ Iso\ vs\ D6}=0.95$; time to 50% relaxation: p-value$_{D0\ vs\ D6}=0.96$, p-value$_{D0\ Iso\ vs\ D6\ Iso}=0.69$; time to 100% relaxation: p-value$_{D0\ vs\ D6}=0.96$, p-value$_{D0\ Iso\ vs\ D6\ Iso}=0.95$). (C) Representative immunofluorescence images showing expression of connexin 43 in cardiomyocytes in longitudinal sections from either fresh heart slices (top panel), slices cultured for 6 days under biomimetic stimulated culture conditions (middle panel), or slices cultured for 6 days under unstimulated transwell conditions (bottom panel), scale bar, 100 μm. (D) Quantification of the area occupied by connexin 43 in fresh heart slices, and heart slices cultured for 6 days either under biomimetic stimulated culture or unstimulated culture (n=2 human hearts, 3 replicates of each, One-Way ANOVA test was conducted to compare between groups; *$p<0.05$ compared to stimulated day 6 group, p-value$_{day\ 0\ vs\ stimulated\ day\ 6}=0.58$).
Figure 6B:
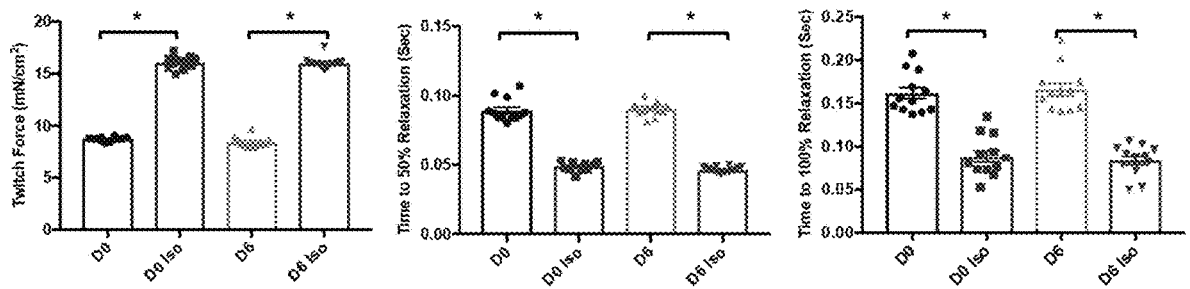
Figure 6C:
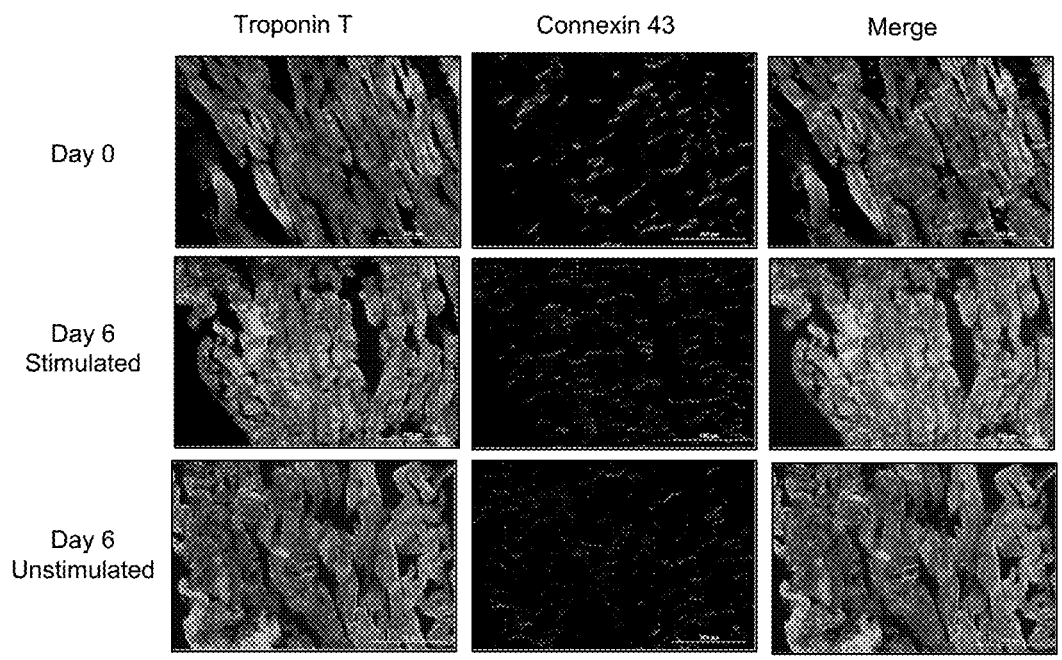
Figure 6D:
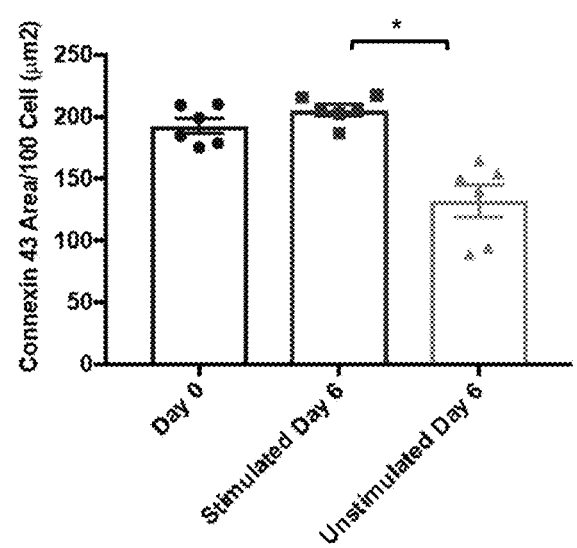

Human Heart Slices Perform Similarly to Porcine Heart Slices in the Biomimetic Stimulated Culture System Our ultimate goal in developing a heart slice culture system is to enable efficacy and toxicity testing of various therapeutics on human heart tissue. Based on the enhanced viability and functionality of pig heart slice provided by our biomimetic stimulated heart slice culture system, we next tested its application to human heart slices. Heart slices derived from donors whose hearts were disqualified for transplantation, because of drug abuse, were received and processed within 12 hours of death. The slices from these healthy hearts performed in a manner similar to the pig heart slices in our biomimetic stimulated culture system. The slices showed 100% viability, similar to fresh slices, for up to day 6 in culture, after which viability declined. By comparison, using the transwell unstimulated culture system, human heart slice viability started to decline as early as day 2 in culture (FIG. 6A). Functionally, the human heart slices cultured for 6 days in the biomimetic stimulated culture system produced twitch force and responses to isoproterenol similar to fresh slices (FIG. 6B). Furthermore, the slices kept in the biomimetic stimulated culture for 6 days showed integrity of connexin 43 at the gap junctions similar to fresh human heart slices. In contrast, slices cultured for 6 days using the transwell culture showed disruption and significant decrease in connexin 43 expression (FIGS. 6C and D).

Genetic Manipulation of Heart Slices to Test Gene Therapy for Heart Failure

Figure 7A:
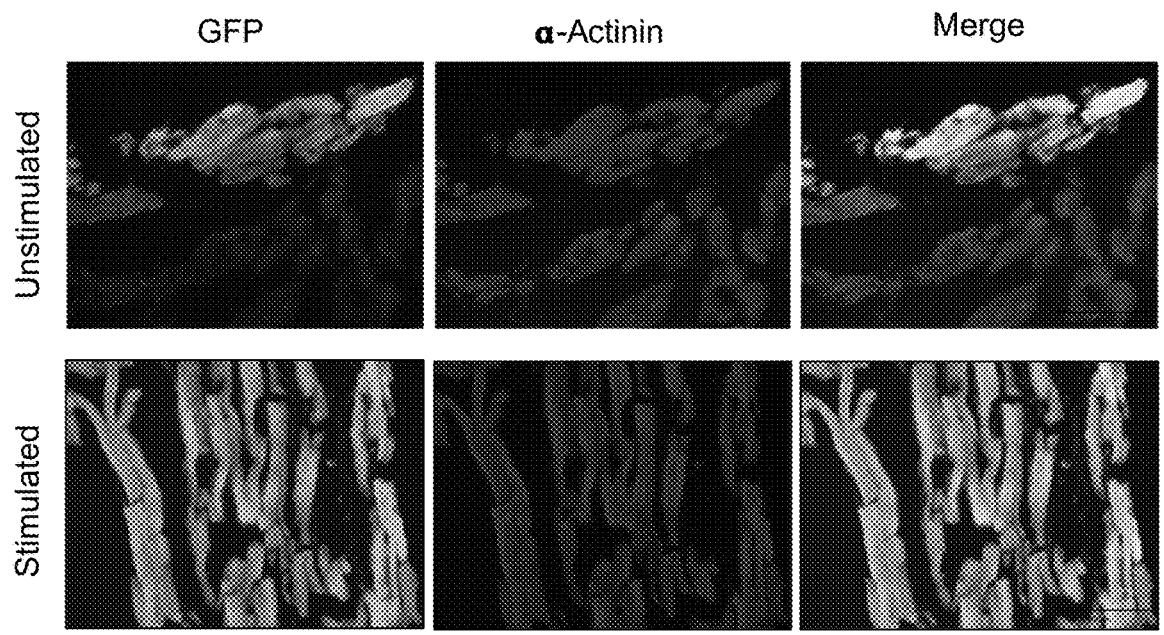
FIG. 7A-D. Genetic manipulation of heart slices in culture. (A) Representative immunofluorescence images showing expression of green fluorescent protein (GFP, green) in cardiomyocytes (red) after 72 hours of infection with adenovirus encoding GFP in unstimulated transwell (top panel) or stimulated (bottom panel) culture system. (B) Representative immunofluorescence images showing the expression of phospho-histone-H3 (PHH3) in cardiomyocytes 72 hours following infection with 4F adenoviruses or LacZ control virus. (C) Quantification of PHH3 positive cardiomyocytes in heart slices infected either with 4F encoding adenovirus or LacZ control (n=2 human hearts each in triplicate, unpaired Student t tests was conducted to compare between groups; *p<0.05). (D) Bar graph showing the quantification of the contractile force generated by heart slices following infection with either 4F or LacZ control adenovirus (n=4 slices each in duplicate, unpaired Student t tests was conducted to compare between groups; *p<0.05).
Figure 7B:
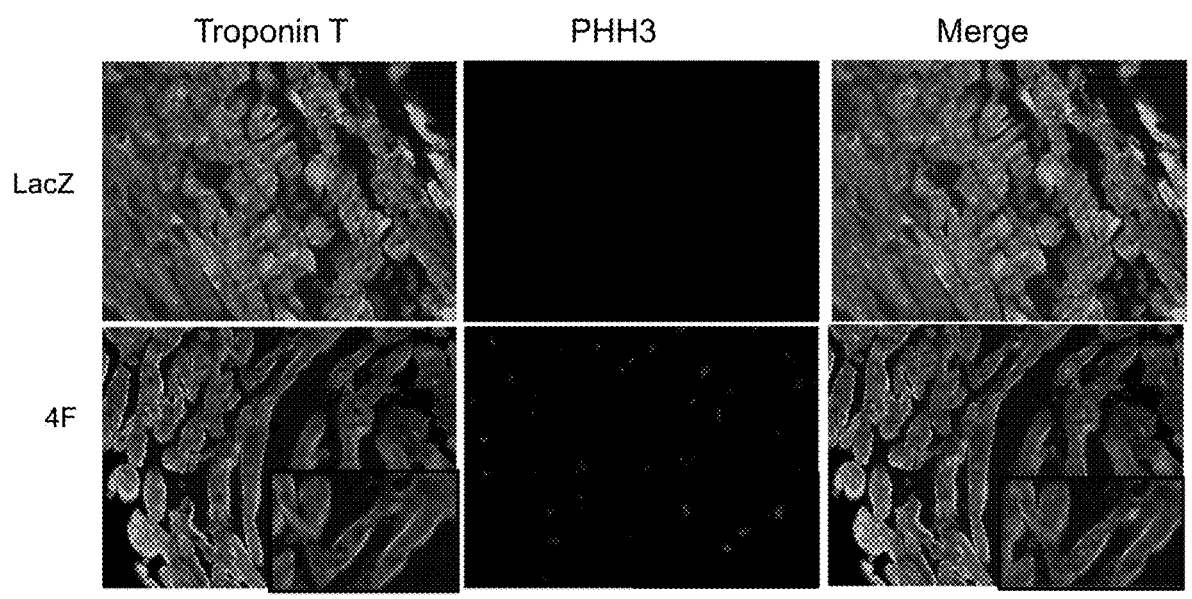
Figure 7C:
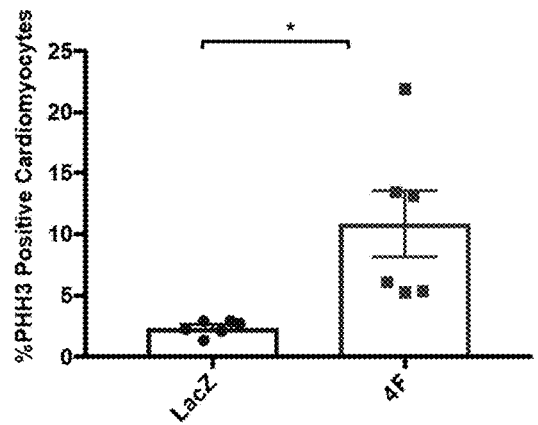
Figure 7D:
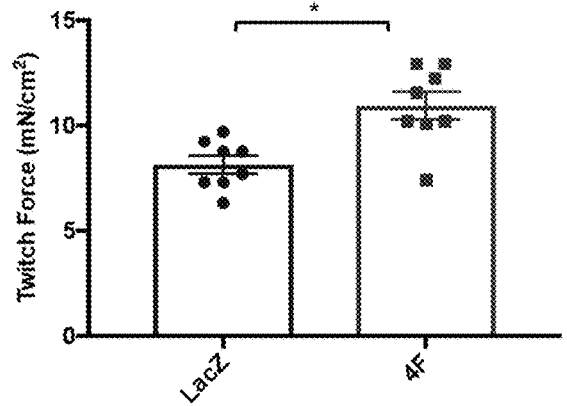
Figure 8A:
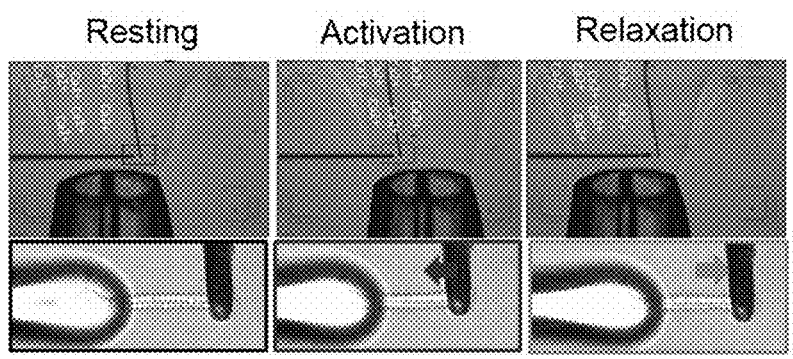
FIG. 8A-D. Myofibril mechanics in cultured heart slices are similar to fresh heart slices. (A) Image of double barrel perfusion pipette delivering different concentrations of calcium. Myofibrils are mounted between a force probe (calibrated to detect force in $\mu N/\mu m$) and a supporting stretcher. (B) Representative images for myofibrils isolated from fresh as well as cultured pig heart slices (left panel). Quantification of resting sarcomere length and resting tension for myofibrils isolated from fresh and cultured heart slices (n=8-13 myofibrils in each group, unpaired Student t tests was conducted to compare between groups). (C) Quantification of myofibril maximal tension, activation kinetic, and reactivation kinetics shows no significant differences between myofibrils isolated from fresh and cultured heart slices (n=10-13 myofibrils in each group, unpaired Student t tests was conducted to compare between groups). (D) Quantification of linear and exponential relaxation phases' kinetics shows no significant difference between the myofilaments isolated from fresh and cultured pig heart slices (n=10-13 in each group, unpaired Student t tests was conducted to compare between groups).
Figure 8B:
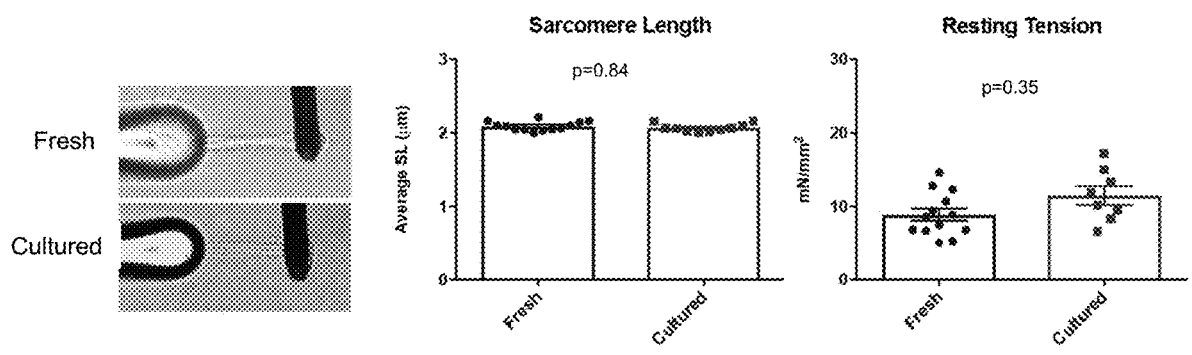
Figure 8C:
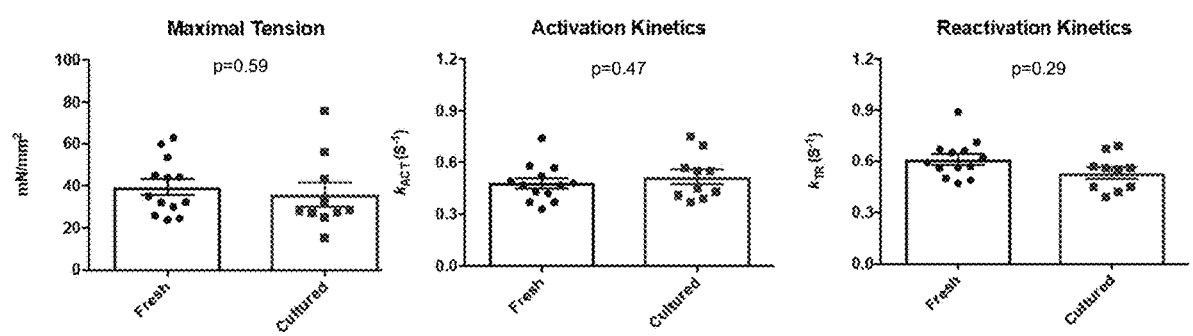
Figure 8D:
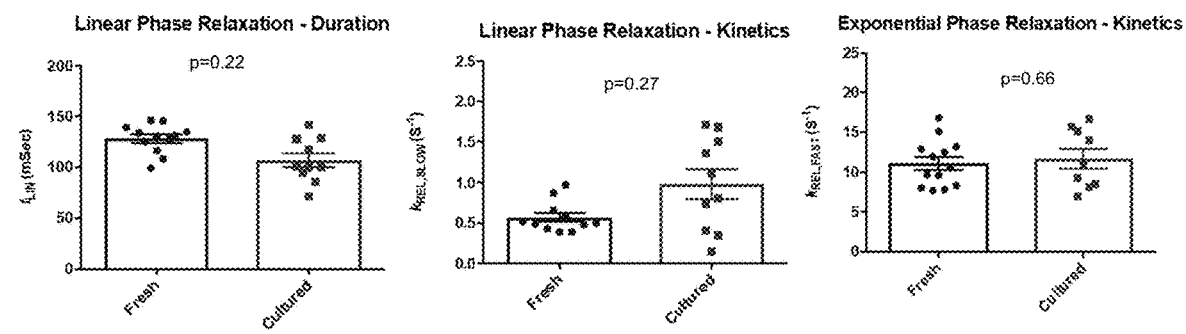

One of the major limitations of existing heart slice technologies is the inability to genetically manipulate them using viral infection. This is mainly due to the nature of the transwell culture and the unavailability of a submerged culture system. To determine whether our biomimetic stimulated culture system would overcome this obstacle, we infected heart slices with adenovirus encoding GFP. We observed only superficial virus penetration in the transwell culture system compared to complete infection in the biomimetic stimulated culture system (FIG. 7A). Based on this successful infection, we performed a study to assess the activity of a potential gene therapy in human heart slices. Recently, we reported that a cocktail of 4 cell cycle factors (CDK1, CDK4, Cyclin D, and Cyclin B) induced adult cardiomyocyte proliferation and functional improvement in mouse hearts[18]. We tested whether infecting human heart slices with adenoviruses encoding these 4 cell cycle factors could also induce human cardiomyocyte proliferation. We observed a significant increase in cardiomyocyte staining for phospho-histone H3, a marker of early proliferation, in slices infected with the 4 cell cycle factors compared to those infected with control virus (FIGS. 7B and C). Functionally, the heart slices infected with the 4 cell cycle factors also showed a significant increase in twitch force compared to those infected with control virus, possibly due to an increase in functional myocyte number and density (FIG. 7D). This is the first demonstration of functional testing of a potential cardiac gene therapy using cultured heart slices.

Assessment of Myofibril Mechanics Isolated from Cultured Heart Slices

It is important to take this heart slice technology to the next level of rigor and accuracy and demonstrate their utility for determining the effect of therapeutics and toxins on single cardiac myofibrils. Therefore, we isolated single myofibrils from fresh hearts and heart slices cultured for 48 hours. While there was unexpected variability in the myofibrils isolated from the heart slices, the myofibrils that were successfully activated had similar parameters to myofibrils isolated from fresh hearts in terms of resting tension, force generation and activation/relaxation kinetics (FIG. 8 A-D). This confirms the suitability of such a culture system to be combined with other technologies to support rigorous assessments that predict the efficacy and toxicity of various potential therapeutics.

Discussion

Here we describe a novel simplified medium throughput method that enables culture of human and pig heart slices for a period sufficiently long to test cardiotoxicity and therapeutic efficacy. The proposed conditions mimic the environment of the heart, including nutrient availability, frequency of electrical stimulation, and oxygenation. We attribute the prolonged viability of heart slices in our biomimetic stimulated culture to our focus on recreating the physiological conditions experienced by the intact heart. This concept is supported by our data showing that electrical stimulation alone, without providing essential nutrients, is not sufficient to maintain heart slice viability. Identification of required medium components was based on recent knowledge gained from culturing human iPSC-CMs and induced cardiomyocytes derived through direct cardiac reprogramming[17, 18, 21]. We found that it is preferable to include FBS in the medium to maintain the viability. This is likely due to the requirement for a variety of proteins, macromolecules, fatty acids, trace elements, enzymes, proteins, chemical components, and hormones, which are usually present in the serum and delivered to heart tissue in vivo[22]. Furthermore, we found that the addition of FGF and VEGF to the medium enhanced tissue viability. FGF and VEGF factors are well known angiogenic factors essential for maintenance of cultured endothelial cells[23]. In addition, they improve the differentiation and maintenance of directly reprogrammed cardiomyocytes[19]. Therefore, it is likely that FGF and VEGF are needed to maintain the endothelial cells as well as cardiomyocytes in culture to support tissue viability. Our work is the first to modify the simplified culture medium previously reported for heart slices.

Three recent studies have demonstrated the importance of continuous electromechanical stimulation in maintaining slices in culture[13-15]. However, all of these studies used the basal M199/ITS medium, which is not sufficient to maintain the metabolic needs of heart slices. This led to several compromises in the slice contractility and calcium homeostasis early during culture[13-15]. Qiao et al.,[13] have shown that using a highly sophisticated bioengineering chips, they can maintain the electrophysiological properties of the heart slices for 4 days, but no assessment of the contractile function was provided. Fischer et al.,[14] have shown that failing human heart slices can be maintained in vitro for up to 4 months when cultured under sub-physiological (0.2 Hz) stimulation auxotonic loading and media agitation in a bioengineering device. However, these non-physiological conditions may induce a variety of changes in the heart slices, as reflected in their RNAseq data, which showed over 10 fold downregulation of cardiac gene expression as early as the first time point of assessment (day 8)[14]. Finally, Watson et al.,[15] have bioengineered a low throughput culture system to demonstrate the importance of diastolic sarcomere length for the maintenance of cardiac muscle properties for 24 hours. For efficient testing of drug toxicity and efficacy of potential therapeutics, it is preferable to perform analyses in a simplified, medium-throughput system under full physiological conditions which could reflect the normal cardiac state. Our biomimetic stimulated culture system emulates the controllable conditions experienced by the heart in situ. Thus, it provides a reliable readout of the functional and the structural outcomes of drug treatment with regard to cardiotoxicity or efficacy compared to compromised culture systems.

Our rigorous assessments show that our biomimetic stimulated culture system maintains viability and functionality of human and pig heart slices for 6 days of culture. However, starting at day 7, we observed cardiomyocytes with spontaneous calcium transients, which is the first sign of dedifferentiation; cell death ensued after day 7. The only early change that we observed in the heart slices in our biomimetic stimulated culture system was a decrease in mitochondrial respiration, leading to a higher reliance on glycolysis for energy. The decrease in oxidative phosphorylation occurred by day 2 in culture; however, glycolysis remained stable until day 8. These changes are expected, given that the culture medium contains low levels of fatty acids, supplied by FBS[24]. The fact that metabolic changes preceded transcriptional changes is consistent with previous findings that indicate the critical role of cellular metabolism in modulating gene expression (as reviewed in [25]). It was interesting that the addition of FGF and VEGF maintained glycolytic capacity of the heart slices for up to 6 days in culture. These findings are in line with the large body of literature showing that FGF and VEGF signaling can influence glycolytic capacity in various cell types[26-30]. Furthermore, the addition of fatty acids to the culture medium significantly reduced connexin 43 expression; this is likely due to their mild solubilization effects on membrane proteins[20]. Nevertheless, it remains possible that genetic manipulation of fatty acid metabolism enzymes or addition of specific fatty acid cocktails is important for extending viability and functionality beyond 6 days. It remains unclear whether the metabolic shift to glycolysis promotes cardiomyocyte dedifferentiation or hastens cell death. It may be that pharmacological agents that promote mitochondrial biogenesis or provision of adjuvant substrates for mitochondrial respiration (e.g., ketones, lactate, fatty acid cocktails) maintain the heart slices in culture for longer periods of time.

This new culture system addresses one of the major limitations of previous heart slice culture systems as it provides a medium-throughput platform to test novel gene therapy approaches in human heart tissue in situ. As described herein, we demonstrate that one of our recently developed gene therapy approaches, which induces cardiomyocyte proliferation in mouse models in vivo, is also effective in activating cardiomyocyte replication in human heart slices. Furthermore, we demonstrated that this technology could be used to assess the effect of therapeutics or toxins on contractile mechanics of single myofibrils. This technology may function as a platform to test the efficacy of novel therapeutic agents for heart failure in intact 3D human heart tissue prior to initiating clinical trials. In addition, our culture platform could be used as a medium-throughput assay to test cardiotoxicity because we can simultaneously culture 8×6 well plates using one C-Pace device. Biochemical assays such as MTT, CK-MB, or LDH could detect overt cardiotoxicity; however, more in-depth functional assessments, such as calcium transients and force production, could be used to test for subtle undesirable drug effects on cardiac function in situ.

In conclusion, our biomimetic stimulated human and pig heart slice culture system is a novel, reliable, and easily reproducible medium-throughput method for testing acute drug cardiotoxicity or efficacy of novel heart failure therapies. Results above show several major advancements over existing methodologies including culture media composition, physiological electrical stimulation, and genetic manipulation of the heart slices.

REFERENCES

1. Writing Group M, Mozaffarian D, Benjamin E J, Go A S, Arnett D K, Blaha M J, Cushman M, Das S R, de Ferranti S, Despres J P, Fullerton H J, Howard V J, Huffman M D, Isasi C R, Jimenez M C, Judd S E, Kissela B M, Lichtman J H, Lisabeth L D, Liu S, Mackey R H, Magid D J, McGuire D K, Mohler E R, 3rd, Moy C S, Muntner P, Mussolino M E, Nasir K, Neumar R W, Nichol G, Palaniappan L, Pandey D K, Reeves M J, Rodriguez C J, Rosamond W, Sorlie P D, Stein J, Towfighi A, Turan T N, Virani S S, Woo D, Yeh R W, Turner M B, American Heart Association Statistics C, Stroke Statistics S. Heart disease and stroke statistics-2016 update: A report from the american heart association. *Circulation.* 2016; 133:e38-360
2. Onakpoya I J, Heneghan C J, Aronson J K. Post-marketing withdrawal of 462 medicinal products because of adverse drug reactions: A systematic review of the world literature. *BMC Med.* 2016; 14:10
3. Robertson C, Tran D D, George S C. Concise review: Maturation phases of human pluripotent stem cell-derived cardiomyocytes. *Stem Cells.* 2013; 31:829-837
4. Ronaldson-Bouchard K, Ma S P, Yeager K, Chen T, Song L, Sirabella D, Morikawa K, Teles D, Yazawa M, Vunjak-Novakovic G. Advanced maturation of human cardiac tissue grown from pluripotent stem cells. *Nature.* 2018; 556:239-243
5. Pinto A R, Ilinykh A, Ivey M J, Kuwabara J T, D'Antoni M L, Debuque R, Chandran A, Wang L, Arora K, Rosenthal N A, Tallquist M D. Revisiting cardiac cellular composition. *Circ Res.* 2016; 118:400-409
6. Kanisicak O, Khalil H, Ivey M J, Karch J, Maliken B D, Correll R N, Brody M J, SC J L, Aronow B J, Tallquist M D, Molkentin J D. Genetic lineage tracing defines myofibroblast origin and function in the injured heart. *Nat Commun.* 2016; 7:12260
7. Fu X, Khalil H, Kanisicak O, Boyer J G, Vagnozzi R J, Maliken B D, Sargent M A, Prasad V, Valiente-Alandi I, Blaxall B C, Molkentin J D. Specialized fibroblast differentiated states underlie scar formation in the infarcted mouse heart. *J Clin Invest.* 2018; 128:2127-2143
8. Kretzschmar K, Post Y, Bannier-Helaouet M, Mattiotti A, Drost J, Basak O, Li V S W, van den Born M, Gunst Q D, Versteeg D, Kooijman L, van der Elst S, van Es J H, van Rooij E, van den Hoff M J B, Clevers H. Profiling proliferative cells and their progeny in damaged murine hearts. *Proc Natl Acad Sci USA.* 2018; 115:E12245-E12254
9. Brandenburger M, Wenzel J, Bogdan R, Richardt D, Nguemo F, Reppel M, Hescheler J, Terlau H, Dendorfer A. Organotypic slice culture from human adult ventricular myocardium. *Cardiovasc Res.* 2012; 93:50-59
10. Perbellini F, Watson S A, Scigliano M, Alayoubi S, Tkach S, Bardi I, Quaife N, Kane C, Dufton N P, Simon A, Sikkel M B, Faggian G, Randi A M, Gorelik J, Harding S E, Terracciano C M. Investigation of cardiac fibroblasts using myocardial slices. *Cardiovasc Res.* 2018; 114:77-89
11. Watson S A, Scigliano M, Bardi I, Ascione R, Terracciano C M, Perbellini F. Preparation of viable adult ventricular myocardial slices from large and small mammals. *Nature protocols.* 2017; 12:2623-2639
12. Kang C, Qiao Y, Li G, Baechle K, Camelliti P, Rentschler S, Efimov I R. Human organotypic cultured cardiac slices: New platform for high throughput preclinical human trials. *Sci Rep.* 2016; 6:28798
13. Qiao Y, Dong Q, Li B, Obaid S, Miccile C, Yin R T, Talapatra T, Lin Z, Li S, Li Z, Efimov I R. Multiparametric slice culture platform for the investigation of human cardiac tissue physiology. *Progress in biophysics and molecular biology.* 2018
14. Fischer C, Milting H, Fein E, Reiser E, Lu K, Seidel T, Schinner C, Schwarzmayr T, Schramm R, Tomasi R, Husse B, Cao-Ehlker X, Pohl U, Dendorfer A. Long-term functional and structural preservation of precision-cut human myocardium under continuous electromechanical stimulation in vitro. *Nat Commun.* 2019; 10:117
15. Watson S A, Duff J, Bardi I, Zabielska M, Atanur S S, Jabbour R J, Simon A, Tomas A, Smolenski R T, Harding S E, Perbellini F, Terracciano C M. Biomimetic electromechanical stimulation to maintain adult myocardial slices in vitro. *Nat Commun.* 2019; 10:2168
16. Crick S J, Sheppard M N, Ho S Y, Gebstein L, Anderson R H. Anatomy of the pig heart: Comparisons with normal human cardiac structure. *J Anat.* 1998; 193 (Pt 1):105-119
17. Mohamed T M, Stone N R, Berry E C, Radzinsky E, Huang Y, Pratt K, Ang Y S, Yu P, Wang H, Tang S, Magnitsky S, Ding S, Ivey K N, Srivastava D. Chemical enhancement of in vitro and in vivo direct cardiac reprogramming *Circulation.* 2017; 135:978-995
18. Mohamed T M A, Ang Y S, Radzinsky E, Zhou P, Huang Y, Elfenbein A, Foley A, Magnitsky S, Srivastava D. Regulation of cell cycle to stimulate adult cardiomyocyte proliferation and cardiac regeneration. *Cell.* 2018; 173:104-116 e112
19. Yamakawa H, Muraoka N, Miyamoto K, Sadahiro T, Isomi M, Haginiwa H, Kojima H, Umei T, Akiyama M, Kuishi Y, Kurokawa J, Furukawa T, Fukuda K, Ieda M. Fibroblast growth factors and vascular endothelial growth factor promote cardiac reprogramming under defined conditions. *Stem Cell Reports.* 2015; 5:1128-1142
20. Ibarguren M, Lopez D J, Escriba P V. The effect of natural and synthetic fatty acids on membrane structure, microdomain organization, cellular functions and human health. *Biochim Biophys Acta.* 2014; 1838: 1518-1528
21. Ang Y S, Rivas R N, Ribeiro A J, Srivas R, Rivera J, Stone N R, Pratt K, Mohamed T M, Fu J D, Spencer C I, Tippens N D, Li M, Narasimha A, Radzinsky E, Moon-Grady A J, Yu H, Pruitt B L, Snyder M P, Srivastava D. Disease model of gata4 mutation reveals transcription factor cooperativity in human cardiogenesis. *Cell.* 2016; 167:1734-1749 e1722
22. Franke J, Abs V, Zizzadoro C, Abraham G. Comparative study of the effects of fetal bovine serum versus horse serum on growth and differentiation of primary equine bronchial fibroblasts. *BMC Vet Res.* 2014; 10:119
23. Vuorenpaa H, Ikonen L, Kujala K, Huttala O, Sarkanen J R, Ylikomi T, Aalto-Setala K, Heinonen T. Novel in vitro cardiovascular constructs composed of vascular-like networks and cardiomyocytes. *In Vitro Cell Dev Biol Anim.* 2014; 50:275-286
24. Stoll L L, Spector A A. Changes in serum influence the fatty acid composition of established cell lines. *In Vitro.* 1984; 20:732-738
25. van der Knaap J A, Verrijzer C P. Undercover: Gene control by metabolites and metabolic enzymes. *Genes Dev.* 2016; 30:2345-2369
26. Yu P, Wilhelm K, Dubrac A, Tung J K, Alves T C, Fang J S, Xie Y, Zhu J, Chen Z, De Smet F, Zhang J, Jin S W, Sun L, Sun H, Kibbey R G, Hirschi K K, Hay N, Carmeliet P, Chittenden T W, Eichmann A, Potente M, Simons M. Fgf-dependent metabolic control of vascular development. *Nature.* 2017; 545:224-228
27. Bradley C A. Fgfr1 reprogrammes cell metabolism. *Nat Rev Urol.* 2018; 15:528
28. Liu J, Chen G, Liu Z, Liu S, Cai Z, You P, Ke Y, Lai L, Huang Y, Gao H, Zhao L, Pelicano H, Huang P, 28. McKeehan W L, Wu C L, Wang C, Zhong W, Wang F. Aberrant fgfr tyrosine kinase signaling enhances the warburg effect by reprogramming ldh isoform expression and activity in prostate cancer. *Cancer Res.* 2018; 78:4459-4470
29. Fitzgerald G, Soro-Arnaiz I, De Bock K. The warburg effect in endothelial cells and its potential as an anti-angiogenic target in cancer. *Front Cell Dev Biol.* 2018; 6:100
30. Shi S, Xu J, Zhang B, Ji S, Xu W, Liu J, Jin K, Liang D, Liang C, Liu L, Liu C, Qin Y, Yu X. Vegf promotes glycolysis in pancreatic cancer via hif1 alpha up-regulation. *Curr Mol Med.* 2016; 16:394-403
31. Jeong M Y, Lin Y H, Wennersten S A, Demos-Davies K M, Cavasin M A, Mahaffey J H, Monzani V, Saripalli C, Mascagni P, Reece T B, Ambardekar A V, Granzier H L, Dinarello C A, McKinsey T A. Histone deacetylase activity governs diastolic dysfunction through a nongenomic mechanism. *Sci Transl Med.* 2018; 10
32. Woulfe K C, Ferrara C, Pioner J M, Mahaffey J H, Coppini R, Scellini B, Ferrantini C, Piroddi N, Tesi C, Poggesi C, Jeong M. A novel method of isolating myofibrils from primary cardiomyocyte culture suitable for myofibril mechanical study. *Front Cardiovasc Med.* 2019; 6:12

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:

1. A method for culturing a mammalian heart organotypic slice, comprising:
   culturing the slice in a culture medium, wherein the culture medium comprises fetal bovine serum (FBS), vascular endothelial cell growth factor (VEGF), fibroblast growth factor (FGF), and insulin-transferrin-selenium (ITS) and wherein the culture medium does not include 2, 3-butanedione monoxime (BDM) or any fatty acids added in addition to fatty acids present in the FBS; and
   applying electrical stimulation to the slice while the heart slice is in culture, wherein the electrical stimulation has a frequency of 0.5 to 2 Hz and wherein the electrical stimulation has a voltage of 5 to 15 V, and wherein a viability of the heart slice measured on day 6 of culturing is not statistically significantly different from a viability of the heart slice measured on day 1 of culturing as measured by MTT assay.
2. The method of claim 1, wherein the electrical stimulation has a frequency of 1.2 Hz.
3. The method of claim 1, wherein the electrical stimulation has a voltage of 10 V.
4. The method of claim 1, wherein a stimulation device used to apply the electrical stimulation comprises graphite electrodes.
5. The method of claim 1, wherein the slice has a thickness of 100-500 μm.
6. The method of claim 1, wherein the culture medium is oxygenated.
7. The method of claim 1, wherein the method is performed for at least 2 days.
8. The method of claim 7, wherein the culture medium is replaced with fresh culture medium at least once per day.
9. The method of claim 1, wherein the mammalian heart slice is obtained from a human or pig.
10. The method of claim 1, wherein the slice is adhered to a support prior to applying the electrical stimulation.
11. The method of claim 1, wherein a contractile force generated by the slice on day 6 of culturing is not statistically significantly different from a contractile force generated by the slice measured on day 1 of culturing.
12. The method of claim 1, wherein the slice does not exhibit any spontaneous calcium transients except upon electrical stimulation.

* * * * *